United States Patent
Popplewell et al.

(10) Patent No.: US 9,970,010 B2
(45) Date of Patent: *May 15, 2018

(54) OLIGOMERS

(71) Applicant: Royal Holloway, University of London, Surrey (GB)

(72) Inventors: Linda Popplewell, Surrey (GB); Ian Graham, Evesham (GB); John George Dickson, Surrey (GB)

(73) Assignee: Royal Holloway, University of London, Egham, Surrey (GB)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/466,631

(22) Filed: Mar. 22, 2017

(65) Prior Publication Data

US 2017/0204413 A1 Jul. 20, 2017

Related U.S. Application Data

(60) Division of application No. 14/736,154, filed on Aug. 24, 2015, now Pat. No. 9,650,632, which is a division of application No. 14/045,841, filed on Oct. 4, 2013, now Pat. No. 9,243,252, which is a continuation of application No. 13/307,926, filed on Nov. 30, 2011, now Pat. No. 8,552,172, which is a division of application No. 12/556,626, filed on Sep. 10, 2009, now Pat. No. 8,084,601.

(60) Provisional application No. 61/164,987, filed on Mar. 31, 2009, provisional application No. 61/096,073, filed on Sep. 11, 2008.

(51) Int. Cl.
| | | |
|---|---|---|
| C07H 21/04 | (2006.01) | |
| C12N 15/113 | (2010.01) | |
| A61K 31/7088 | (2006.01) | |

(52) U.S. Cl.
CPC ........ *C12N 15/113* (2013.01); *A61K 31/7088* (2013.01); *C12N 2310/11* (2013.01); *C12N 2310/321* (2013.01); *C12N 2310/3233* (2013.01); *C12N 2310/351* (2013.01)

(58) Field of Classification Search
None
See application file for complete search history.

(56) References Cited

U.S. PATENT DOCUMENTS

| 7,314,750 | B2 | 1/2008 | Zhou |
|---|---|---|---|
| 8,232,384 | B2 | 7/2012 | Wilton et al. |
| 8,324,371 | B2 | 12/2012 | Popplewell et al. |
| 8,361,979 | B2 | 1/2013 | Aartsma-Rus et al. |
| 8,461,325 | B2 | 6/2013 | Popplewell et al. |
| 8,552,172 | B2 | 10/2013 | Popplewell et al. |
| 9,079,934 | B2 | 7/2015 | Watanabe et al. |
| 9,243,251 | B2 | 1/2016 | Popplewell et al. |
| 9,243,252 | B2 | 1/2016 | Popplewell et al. |
| 9,650,632 | B2 | 5/2017 | Popplewell et al. |
| 9,708,361 | B2 | 7/2017 | Watanabe et al. |
| 2006/0099616 | A1 | 5/2006 | van Ommen et al. |
| 2007/0050146 | A1 | 3/2007 | Bentwich et al. |
| 2009/0099066 | A1 | 4/2009 | Moulton et al. |
| 2011/0263662 | A1 | 10/2011 | De Kimpe et al. |
| 2011/0294753 | A1 | 12/2011 | De Kimpe et al. |
| 2012/0059042 | A1 | 3/2012 | Platenburg et al. |
| 2013/0211062 | A1 | 8/2013 | Watanabe et al. |
| 2015/0166995 | A1 | 6/2015 | Watanabe et al. |
| 2016/0024500 | A1 | 1/2016 | Popplewell et al. |
| 2017/0320903 | A1 | 11/2017 | Watanabe et al. |

FOREIGN PATENT DOCUMENTS

| WO | WO-2002/024906 | | 3/2002 |
|---|---|---|---|
| WO | WO-2004/083432 | A1 | 9/2004 |
| WO | WO-2006/000057 | A1 | 1/2006 |
| WO | WO-2009/147368 | A1 | 12/2009 |
| WO | WO-2012/029986 | A1 | 3/2012 |

OTHER PUBLICATIONS

Aartsma-Rus, A. et al., Antisense-mediated exon skipping: a versatile tool with therapeutic and research applications, RNA, 13:1609-1624 (2007).
Adams et al., Antisense oligonucleotide induced exon skipping and the dystrophin gene transcript: cocktails and chemistries, BMC Molecular Biology, 8:57-64 (2007).
Alter et al., Systemic delivery of morpholino oligonucleotide restores dystrophin expression bodywide and improves dystrophic pathology, Nature Medicine, 12:175-177 (2006).
McClorey et al., Antisense oligonuceotide-induced exon skipping restores dystrophin expression in vitro in a canine model of DMD, 13:1375-1381 (2006).
Popplewell, L., et al., Design of Phosphorodiamidate Morpholino Oligomers (PMOs) for the Induction of Exon Skipping of the Human DMD Gene, British Society for Gene & Cell Therapy, Apr. 7-9, 2008.

*Primary Examiner* — Kimberly Chong
(74) *Attorney, Agent, or Firm* — Choate, Hall & Stewart LLP

(57) ABSTRACT

Molecules are provided for inducing or facilitating exon skipping in forming spliced mRNA products from pre-mRNA molecules in cells. The molecules may be provided directly as oligonucleotides or expression products of vectors that are administered to a subject. High rates of skipping can be achieved. High rates of skipping reduce the severity of a disease like Duchene Muscular Dystrophy so that the disease is more like Becker Muscular Dystrophy. This is a severe reduction in symptom severity and mortality.

14 Claims, 11 Drawing Sheets

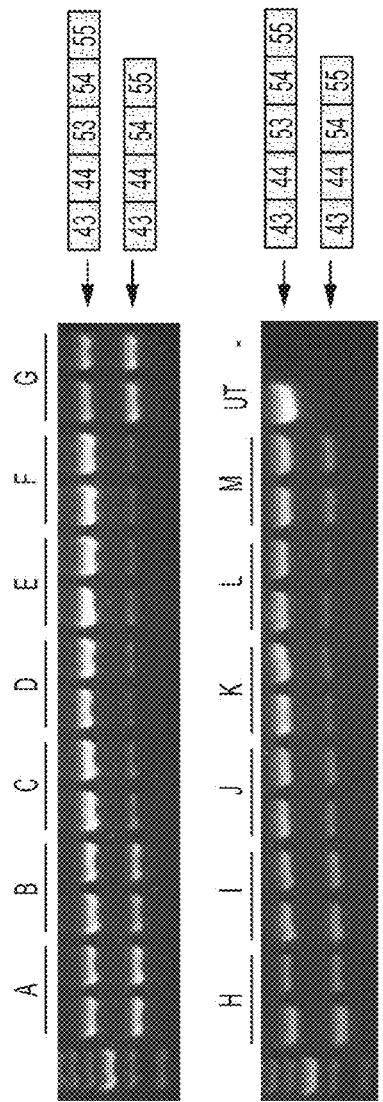
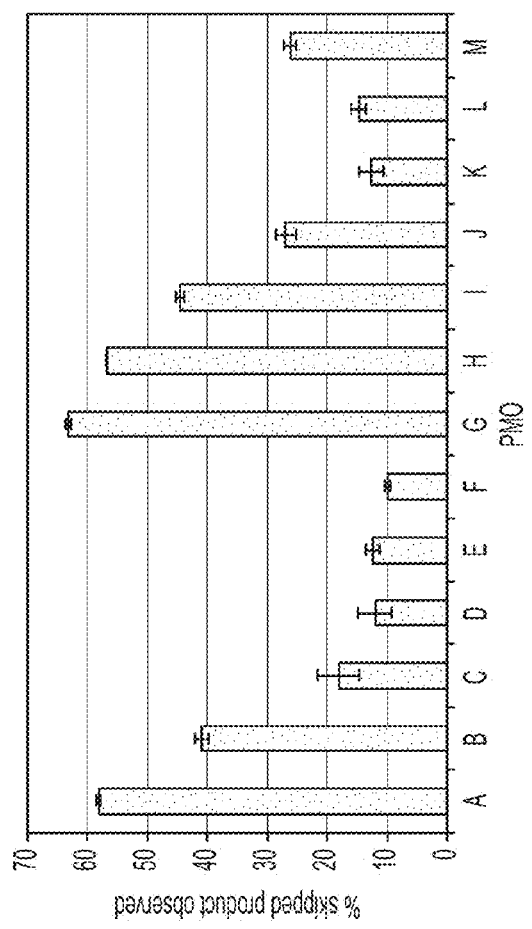
FIG. 8A
FIG. 8B

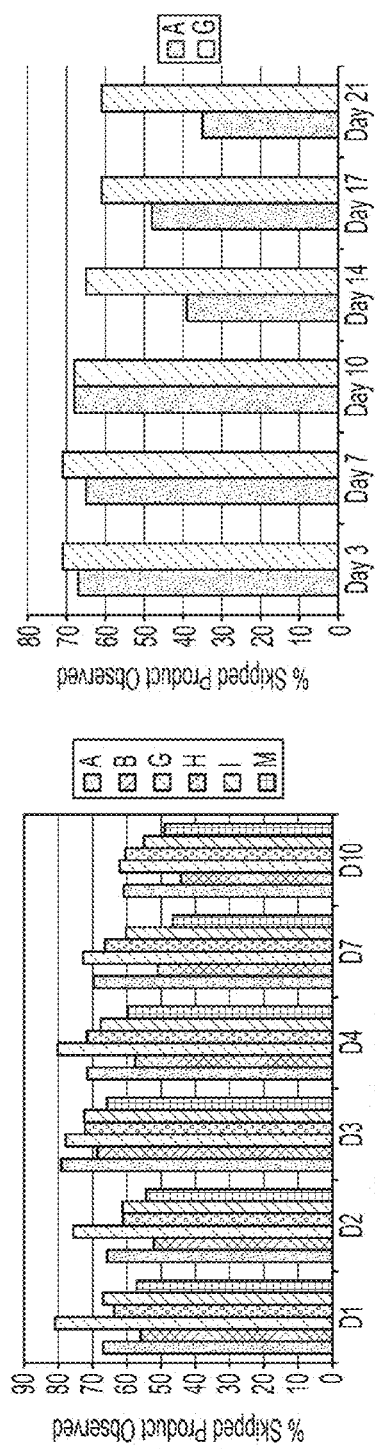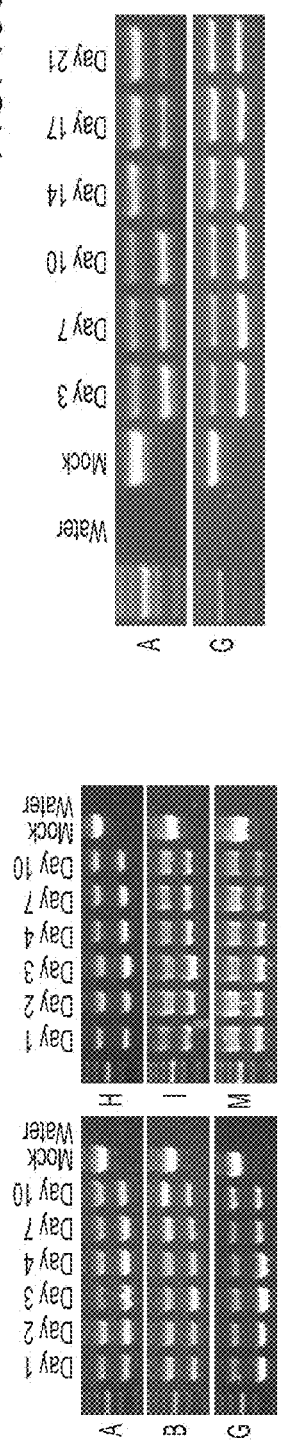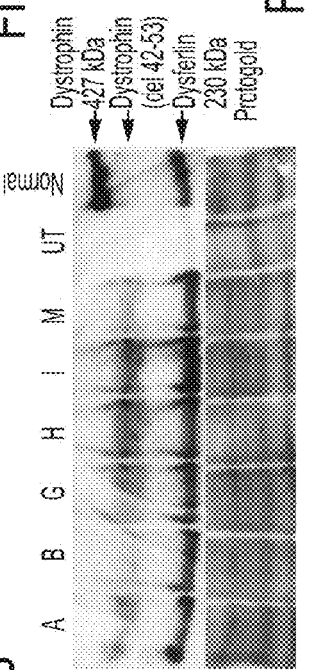

SEQUENCE LISTING

```
<160> NUMBER OF SEQ ID NOS: 26

<210> SEQ ID NO 1
<211> LENGTH: 30
<212> TYPE: DNA
<213> ORGANISM: Artificial Sequence
<220> FEATURE:
<223> OTHER INFORMATION: oligonucleotides or oligonribonucleotides or
      analogs thereof, especially with same base
      sequence
<221> NAME/KEY: misc_feature
<222> LOCATION: (1)...(30)
<223> OTHER INFORMATION: n = T or U

<400> SEQUENCE: 1
ngaaaacgcc gccannncnc aacagancng                                          30

<210> SEQ ID NO 2
<211> LENGTH: 30
<212> TYPE: DNA
<213> ORGANISM: Artificial Sequence
<220> FEATURE:
<223> OTHER INFORMATION: oligonucleotides or oligonribonucleotides or
      analogs thereof, especially with same base
      sequence
<221> NAME/KEY: misc_feature
<222> LOCATION: (1)...(30)
<223> OTHER INFORMATION: n =  T or U

<400> SEQUENCE: 2
canaangaaa acgccgccan nncncaacag                                          30
```

```
<210> SEQ ID NO 3
<211> LENGTH: 30
<212> TYPE: DNA
<213> ORGANISM: Artificial Sequence
<220> FEATURE:
<223> OTHER INFORMATION: oligonucleotides or oligoribonucleotides or
      analogs thereof, especially with same base
      sequence
<221> NAME/KEY: misc_feature
<222> LOCATION: (1)...(30)
<223> OTHER INFORMATION: n = T or U

<400> SEQUENCE: 3
ngnncagcnn cngnnagcca cngannaaan                                              30

<210> SEQ ID NO 4
<211> LENGTH: 30
<212> TYPE: DNA
<213> ORGANISM: Artificial Sequence
<220> FEATURE:
<223> OTHER INFORMATION: oligonucleotides or oligoribonucleotides or
      analogs thereof, especially with same base
      sequence
<221> NAME/KEY: misc_feature
<222> LOCATION: (1)...(30)
<223> OTHER INFORMATION: n = T or U

<400> SEQUENCE: 4
cagnnngccg cngcccaang ccanccngga                                              30

<210> SEQ ID NO 5
<211> LENGTH: 30
<212> TYPE: DNA
<213> ORGANISM: Artificial Sequence
<220> FEATURE:
<223> OTHER INFORMATION: oligonucleotides or oligoribonucleotides or
      analogs thereof, especially with same base
      sequence
<221> NAME/KEY: misc_feature
<222> LOCATION: (1)...(30)
<223> OTHER INFORMATION: n = T or U

<400> SEQUENCE: 5
nngccgcngc ccaangccan ccnggagnnc                                              30

<210> SEQ ID NO 6
<211> LENGTH: 30
<212> TYPE: DNA
<213> ORGANISM: Artificial Sequence
<220> FEATURE:
<223> OTHER INFORMATION: oligonucleotides or oligoribonucleotides or
      analogs thereof, especially with same base
      sequence
<221> NAME/KEY: misc_feature
<222> LOCATION: (1)...(30)
<223> OTHER INFORMATION: n = T or U

<400> SEQUENCE: 6
ngcngcncnn nnccaggnnc aagngggana                                              30

<210> SEQ ID NO 7
<211> LENGTH: 30
<212> TYPE: DNA
<213> ORGANISM: Artificial Sequence
<220> FEATURE:
<223> OTHER INFORMATION: oligonucleotides or oligoribonucleotides or
      analogs thereof, especially with same base
      sequence
<221> NAME/KEY: misc_feature
<222> LOCATION: (1)...(30)
<223> OTHER INFORMATION: n = T or U
```

-continued

<400> SEQUENCE: 7
cnnnnagnng cngcncnnnn ccaggnncaa                                           30

<210> SEQ ID NO 8
<211> LENGTH: 30
<212> TYPE: DNA
<213> ORGANISM: Artificial Sequence
<220> FEATURE:
<223> OTHER INFORMATION: oligonucleotides or oligonribonucleotides or
      analogs thereof, especially with same base
      sequence
<221> NAME/KEY: misc_feature
<222> LOCATION: (1)...(30)
<223> OTHER INFORMATION: n = T or U

<400> SEQUENCE: 8
cnnnncnnnn agnngcngcn cnnnnccagg                                           30

<210> SEQ ID NO 9
<211> LENGTH: 30
<212> TYPE: DNA
<213> ORGANISM: Artificial Sequence
<220> FEATURE:
<223> OTHER INFORMATION: oligonucleotides or oligonribonucleotides or
      analogs thereof, especially with same base
      sequence
<221> NAME/KEY: misc_feature
<222> LOCATION: (1)...(30)
<223> OTHER INFORMATION: n = T or U

<400> SEQUENCE: 9
nnagnngcng cncnnnncca ggnncaagng                                           30

<210> SEQ ID NO 10
<211> LENGTH: 30
<212> TYPE: DNA
<213> ORGANISM: Artificial Sequence
<220> FEATURE:
<223> OTHER INFORMATION: oligonucleotides or oligonribonucleotides or
      analogs thereof, especially with same base
      sequence
<221> NAME/KEY: misc_feature
<222> LOCATION: (1)...(30)
<223> OTHER INFORMATION: n = T or U

<400> SEQUENCE: 10
cngnngccnc cggnncngaa ggngnncnng                                           30

<210> SEQ ID NO 11
<211> LENGTH: 30
<212> TYPE: DNA
<213> ORGANISM: Artificial Sequence
<220> FEATURE:
<223> OTHER INFORMATION: oligonucleotides or oligonribonucleotides or
      analogs thereof, especially with same base
      sequence
<221> NAME/KEY: misc_feature
<222> LOCATION: (1)...(30)
<223> OTHER INFORMATION: n = T or U

<400> SEQUENCE: 11
caacngnngc cnccggnncn gaaggngnnc                                           30

<210> SEQ ID NO 12
<211> LENGTH: 30
<212> TYPE: DNA
<213> ORGANISM: Artificial Sequence

```
<220> FEATURE:
<223> OTHER INFORMATION: oligonucleotides or oligonribonucleotides or
      analogs thereof, especially with same base
      sequence
<221> NAME/KEY: misc_feature
<222> LOCATION: (1)...(30)
<223> OTHER INFORMATION: n =  T or U

<400> SEQUENCE: 12
nngccnccgg nncngaaggn gnncnngnac                                      30

<210> SEQ ID NO 13
<211> LENGTH: 30
<212> TYPE: DNA
<213> ORGANISM: Artificial Sequence
<220> FEATURE:
<223> OTHER INFORMATION: oligonucleotides or oligonribonucleotides or
      analogs thereof, especially with same base
      sequence

<400> SEQUENCE: 13
tgaaaacgcc gccatttctc aacagatctg                                      30

<210> SEQ ID NO 14
<211> LENGTH: 30
<212> TYPE: DNA
<213> ORGANISM: Artificial Sequence
<220> FEATURE:
<223> OTHER INFORMATION: oligonucleotides or oligonribonucleotides or
      analogs thereof, especially with same base
      sequence

<400> SEQUENCE: 14
cataatgaaa acgccgccat ttctcaacag                                      30

<210> SEQ ID NO 15
<211> LENGTH: 30
<212> TYPE: DNA
<213> ORGANISM: Artificial Sequence
<220> FEATURE:
<223> OTHER INFORMATION: oligonucleotides or oligonribonucleotides or
      analogs thereof, especially with same base
      sequence

<400> SEQUENCE: 15
tgttcagctt ctgttagcca ctgattaaat                                      30

<210> SEQ ID NO 16
<211> LENGTH: 30
<212> TYPE: DNA
<213> ORGANISM: Artificial Sequence
<220> FEATURE:
<223> OTHER INFORMATION: oligonucleotides or oligonribonucleotides or
      analogs thereof, especially with same base
      sequence

<400> SEQUENCE: 16
cagtttgccg ctgcccaatg ccatcctgga                                      30

<210> SEQ ID NO 17
<211> LENGTH: 30
<212> TYPE: DNA
<213> ORGANISM: Artificial Sequence
<220> FEATURE:
<223> OTHER INFORMATION: oligonucleotides or oligonribonucleotides or
      analogs thereof, especially with same base
      sequence
```

<400> SEQUENCE: 17
ttgccgctgc ccaatgccat cctggagttc                                    30

<210> SEQ ID NO 18
<211> LENGTH: 30
<212> TYPE: DNA
<213> ORGANISM: Artificial Sequence
<220> FEATURE:
<223> OTHER INFORMATION: oligonucleotides or oligonribonucleotides or
      analogs thereof, especially with same base
      sequence

<400> SEQUENCE: 18
tgctgctctt ttccaggttc aagtgggata                                    30

<210> SEQ ID NO 19
<211> LENGTH: 30
<212> TYPE: DNA
<213> ORGANISM: Artificial Sequence
<220> FEATURE:
<223> OTHER INFORMATION: oligonucleotides or oligonribonucleotides or
      analogs thereof, especially with same base
      sequence

<400> SEQUENCE: 19
cttttagttg ctgctctttt ccaggttcaa                                    30

<210> SEQ ID NO 20
<211> LENGTH: 30
<212> TYPE: DNA
<213> ORGANISM: Artificial Sequence
<220> FEATURE:
<223> OTHER INFORMATION: oligonucleotides or oligonribonucleotides or
      analogs thereof, especially with same base
      sequence

<400> SEQUENCE: 20
cttttctttt agttgctgct cttttccagg                                    30

<210> SEQ ID NO 21
<211> LENGTH: 30
<212> TYPE: DNA
<213> ORGANISM: Artificial Sequence
<220> FEATURE:
<223> OTHER INFORMATION: oligonucleotides or oligonribonucleotides or
      analogs thereof, especially with same base
      sequence

<400> SEQUENCE: 21
ttagttgctg ctcttttcca ggttcaagtg                                    30

<210> SEQ ID NO 22
<211> LENGTH: 30
<212> TYPE: DNA
<213> ORGANISM: Artificial Sequence
<220> FEATURE:
<223> OTHER INFORMATION: oligonucleotides or oligonribonucleotides or
      analogs thereof, especially with same base
      sequence

<400> SEQUENCE: 22
ctgttgcctc cggttctgaa ggtgttcttg                                    30

```
<210> SEQ ID NO 23
<211> LENGTH: 30
<212> TYPE: DNA
<213> ORGANISM: Artificial Sequence
<220> FEATURE:
<223> OTHER INFORMATION: oligonucleotides or oligonribonucleotides or
      analogs thereof, especially with same base
      sequence

<400> SEQUENCE: 23
caactgttgc ctccggttct gaaggtgttc                                        30

<210> SEQ ID NO 24
<211> LENGTH: 30
<212> TYPE: DNA
<213> ORGANISM: Artificial Sequence
<220> FEATURE:
<223> OTHER INFORMATION: oligonucleotides or oligonribonucleotides or
      analogs thereof, especially with same base
      sequence

<400> SEQUENCE: 24
ttgcctccgg ttctgaaggt gttcttgtac                                        30

<210> SEQ ID NO 25
<211> LENGTH: 210
<212> TYPE: DNA
<213> ORGANISM: Artificial Sequence
<220> FEATURE:
<223> OTHER INFORMATION: oligonucleotides or oligonribonucleotides or
      analogs thereof, especially with same base
      sequence

<400> SEQUENCE: 25
tgaaagaatt cagaatcagt gggatgaagt acaagaacac cttcagaacc ggaggcaaca       60
gttgaatgaa atgttaaagg attcaacaca atggctggaa gctaaggaag aagctgagca      120
ggtcttagga caggccagag ccaagcttga gtcatggaag gagggtccct atacagtaga      180
tgcaatccaa aagaaaatca cagaaaccaa                                       210

<210> SEQ ID NO 26
<211> LENGTH: 311
<212> TYPE: DNA
<213> ORGANISM: Artificial Sequence
<220> FEATURE:
<223> OTHER INFORMATION: oligonucleotides or oligonribonucleotides or
      analogs thereof, especially with same base
      sequence

<400> SEQUENCE: 26
cctccagact agcatttact actatatatt tattttttcct tttattctag ttgaaagaat      60
tcagaatcag tgggatgaag tacaagaaca ccttcagaac cggaggcaac agttgaatga     120
aatgttaaag gattcaacac aatggctgga agctaaggaa gaagctgagc aggtcttagg     180
acaggccaga gccaagcttg agtcatggaa ggagggtccc tatacagtag atgcaatcca     240
aaagaaaatc acagaaacca aggttagtat caaagaacct ttttaaaata aaatactggt     300
tacatttgat a                                                          311
```

OLIGOMERS

CROSS REFERENCE TO RELATED APPLICATIONS

This application is a divisional of U.S. Non-Provisional application Ser. No. 14/736,154, filed on Aug. 24, 2015, which is a divisional of U.S. Non-Provisional application Ser. No. 14/045,841, filed on Oct. 4, 2013, now U.S. Pat. No. 9,243,252, which is a continuation of U.S. Non-Provisional application Ser. No. 13/307,926, filed Nov. 30, 2011, now U.S. Pat. No. 8,552,172, which is a divisional of U.S. Non-Provisional application Ser. No. 12/556,626, filed Sep. 10, 2009, now U.S. Pat. No. 8,084,601, which application claims the benefit under 35 USC § 119(e) of U.S. Provisional Application Ser. No. 61/164,978, filed Mar. 31, 2009, and U.S. Provisional Application Ser. No. 61/096,073, filed Sep. 11, 2008, each of which is hereby incorporated by reference in its entirety.

SEQUENCE LISTING

The instant application contains a Sequence Listing that has been submitted electronically in ASCII format and is hereby incorporated by reference in its entirety. The ASCII copy, created on Mar. 23, 2017, is named 2006685 1496 SL.TXT and is 12,888 bytes in size.

TECHNICAL FIELD OF THE INVENTION

The present invention relates to molecules which are capable of causing exon skipping and, in particular, relates to molecules which are capable of causing exon skipping in the dystrophin gene.

BACKGROUND OF THE INVENTION

Duchenne muscular dystrophy (DMD) is a severe X-linked muscle wasting disease, affecting 1:3500 boys. Prognosis is poor: loss of mobility by the age of 12, compromised respiratory and cardiac function by late teens, and probable death by the age of 30. The disease is caused by mutations within the large dystrophin gene, such that the reading frame is disrupted leading to lack of dystrophin protein expression and breakdown of muscle fibre integrity [1]. The dystrophin gene is large, with 79 exons. The most common DMD mutation is genomic deletion of one or more exons, generally centred around hotspots involving exons 44 to 55 and the 5' end of the gene [2]. Mutations of the dystrophin gene that preserve the reading frame result in the milder, non-life threatening Becker muscular dystrophy (BMD).

Exon skipping induced by antisense oligoribonucleotides (AOs), generally based on an RNA backbone, is a future hope as a therapy for DMD in which the effects of mutations in the dystrophin gene can be modulated through a process of targeted exon skipping during the splicing process. The splicing process is directed by complex multi-particle machinery that brings adjacent exon-intron junctions in pre-mRNA into close proximity and performs cleavage of phosphodiester bonds at the ends of the introns with their subsequent reformation between exons that are to be spliced together. This complex and highly precise process is mediated by sequence motifs in the pre-mRNA that are relatively short semi-conserved RNA segments to which bind the various nuclear splicing factors that are then involved in the splicing reactions. By changing the way the splicing machinery reads or recognises the motifs involved in pre-mRNA processing, it is possible to create differentially spliced mRNA molecules.

It has now been recognised that the majority of human genes are alternatively spliced during normal gene expression, although the mechanisms involved have not been identified. Using antisense oligonucleotides, it has been shown that errors and deficiencies in a coded mRNA could be bypassed or removed from the mature gene transcripts. Indeed, by skipping out-of-frame mutations of the dystrophin gene, the reading frame can be restored and a truncated, yet functional, Becker-like dystrophin protein is expressed. Studies in human cells in vitro [3, 4] and in animal models of the disease in vivo [5-9] have proven the principle of exon skipping as a potential therapy for DMD (reviewed in [10]). Initial clinical trials using two different AO chemistries (phosphorodiamidate morpholino oligomer (PMO) and phosphorothioate-linked 2'-O-methyl RNA (2'OMePS)) [11] have recently been performed, with encouraging results. Indisputably impressive restoration of dystrophin expression in the TA muscle of four DMD patients injected with a 2'OMePS AO to exon 51 has been reported by van Deutekom et al. [11].

However, it should be noted that, relative to 2'OMePS AOs, PMOs have been shown to produce more consistent and sustained exon skipping in the mdx mouse model of DMD [12-14; A. Malerba et al, manuscript submitted], in human muscle explants [15], and in dystrophic canine cells in vitro [16]. Most importantly, PMOs have excellent safety profiles from clinical and pre-clinical data [17].

The first step to a clinical trial is the choice of the optimal AO target site for skipping of those dystrophin exons most commonly deleted in DMD. In depth analysis of arrays of 2'OMePS AOs have been reported [18, 19], and relationships between skipping bioactivity and AO variables examined.

One problem associated with the prior art is that the antisense oligonucleotides of the prior art do not produce efficient exon skipping. This means that a certain amount of mRNA produced in the splicing process will contain the out-of-frame mutation which leads to protein expression associated with DMD rather than expression of the truncated, yet functional, Becker-like dystrophin protein associated with mRNA in which certain exons have been skipped.

Another problem associated with the prior art is that antisense oligonucleotides have not been developed to all of the exons in the dystrophin gene in which mutations occur in DMD.

An aim of the present invention is to provide molecules which cause efficient exon skipping in selected exons of the dystrophin gene, thus being suitable for use in ameliorating the effects of DMD.

SUMMARY OF THE INVENTION

The present invention relates to molecules which can bind to pre-mRNA produced from the dystrophin gene and cause a high degree of exon skipping in a particular exon. These molecules can be administered therapeutically.

The present invention provides a molecule for ameliorating DMD, the molecule comprising at least a 25 base length from a base sequence selected from:

a)
(SEQ ID NO: 1)
XGA AAA CGC CGC CAX XXC XCA ACA GAX CXG;

b)
(SEQ ID NO: 2)
CAX AAX GAA AAC GCC GCC AXX XCX CAA CAG;

c)
(SEQ ID NO: 3)
XGX XCA GCX XCX GXX AGC CAC XGA XXA AAX;

d)
(SEQ ID NO: 4)
CAG XXX GCC GCX GCC CAA XGC CAX CCX GGA;

e)
(SEQ ID NO: 5)
XXG CCG CXG CCC AAX GCC AXC CXG GAG XXC;

f)
(SEQ ID NO: 6)
XGC XGC XCX XXX CCA GGX XCA AGX GGG AXA;

g)
(SEQ ID NO: 7)
CXX XXA GXX GCX GCX CXX XXC CAG GXX CAA;

h)
(SEQ ID NO: 8)
CXX XXC XXX XAG XXG CXG CXC XXX XCC AGG;

i)
(SEQ ID NO: 9)
XXA GXX GCX GCX CXX XXC CAG GXX CAA GXG;

j)
(SEQ ID NO: 10)
CXG XXG CCX CCG GXX CXG AAG GXG XXC XXG;

k)
(SEQ ID NO: 11)
CAA CXG XXG CCX CCG GXX CXG AAG GXG XXC;
or l)
(SEQ ID NO: 12)
XXG CCX CCG GXX CXG AAG GXG XXC XXG XAC, wherein the molecule's base sequence can vary from the above sequence at up to two base positions, and wherein the molecule can bind to a target site to cause exon skipping in an exon of the dystrophin gene.

The exon of the dystrophin gene is selected from exons 44, 45, 46 or 53. More specifically, the molecule that causes skipping in exon 44 comprises at least a 25 base length from a base sequence selected from:

a)
(SEQ ID NO: 1)
XGA AAA CGC CGC CAX XXC XCA ACA GAX CXG;

b)
(SEQ ID NO: 2)
CAX AAX GAA AAC GCC GCC AXX XCX CAA CAG;
or c)
(SEQ ID NO: 3)
XGX XCA GCX XCX GXX AGC CAC XGA XXA AAX, wherein the molecule's sequence can vary from the above sequence at up to two base positions, and wherein the molecule can bind to a target site to cause exon skipping in exon 44 of the dystrophin gene.

The molecule that causes skipping in exon 45 comprises at least a 25 base length from a base sequence selected from:

d)
(SEQ ID NO: 4)
CAG XXX GCC GCX GCC CAA XGC CAX CCX GGA;
or e)
(SEQ ID NO: 5)
XXG CCG CXG CCC AAX GCC AXC CXG GAG XXC, wherein the molecule's sequence can vary from the above sequence at up to two base positions, and wherein the molecule can bind to a target site to cause exon skipping in exon 45 of the dystrophin gene.

The molecule that causes skipping in exon 46 comprises at least a 25 base length from a base sequence selected from:

f)
(SEQ ID NO: 6)
XGC XGC XCX XXX CCA GGX XCA AGX GGG AXA;

g)
(SEQ ID NO: 7)
CXX XXA GXX GCX GCX CXX XXC CAG GXX CAA;

h)
(SEQ ID NO: 8)
CXX XXC XXX XAG XXG CXG CXC XXX XCC AGG;
or i)
(SEQ ID NO: 9)
XXA GXX GCX GCX CXX XXC CAG GXX CAA GXG, wherein the molecule's sequence can vary from the above sequence at up to two base positions, and wherein the molecule can bind to a target site to cause exon skipping in exon 46 of the dystrophin gene.

The molecule that causes skipping in exon 53 comprises at least a 25 base length from a base sequence selected from:

j)
(SEQ ID NO: 10)
CXG XXG CCX CCG GXX CXG AAG GXG XXC XXG;

k)
(SEQ ID NO: 11)
CAA CXG XXG CCX CCG GXX CXG AAG GXG XXC;
or l)
(SEQ ID NO: 12)
XXG CCX CCG GXX CXG AAG GXG XXC XXG XAC, wherein the molecule's sequence can vary from the above sequence at up to two base positions, and wherein the molecule can bind to a target site to cause exon skipping in exon 53 of the dystrophin gene.

BRIEF DESCRIPTION OF THE DRAWINGS

(FIG. 1A) Results of ESEfinder analysis, showing the location and values above threshold for SF2/ASF, SF2/ASF (BRCA1), SC35, SRp40 and SRp55, shown as grey and black bars, as indicated in the legend above. (FIG. 1B) Output of PESX analysis, showing the location of exonic splicing enhancers as solid lines, and exonic splicing silencer as a dashed line. (FIG. 1C) Rescue ESE analysis for exon 53, showing predicted ESEs by lines, and where they overlap, by a ladder of lines. (FIG. 1D) AccessMapper analysis of in vitro hybridization. Synthetic pre-mRNA containing exon 53 and surrounding introns was subjected to a hybridization screen against a random hexamer oligonucleotide array, as described in Materials and Methods. Areas of hybridization, suggestive of areas of open conformation, are indicated by peaks on the graph. (FIG. 1E) The position of the target sites of two 2'OMePS AOs studied previously [18] are shown for comparison. (FIG. 1F) The location of the target sites for all the 25 mer and 30 mer PMOs to exon 53 used in this study are indicated by lines, and numbered according to the scheme used in Table 1, except for exclusion of the prefix "h53";

(FIG. 7A) hSkMC myoblasts were transfected with the PMOs indicated over a concentration range of 25 nM to 100 nM using lipofectin (1:4). RNA was harvested after 24 hours and subjected to nested RT-PCR, and products visualised by agarose gel electrophoresis. (FIG. 7B) hSkMC myoblasts were transfected with 100 nM and 500 nM concentrations of PMO-G (+30+59) using lipofectin. RNA was harvested at the timepoints indicated following transfection and subjected to nested RT-PCR, and products visualised by agarose gel electrophoresis. Skipped (248 bp) and unskipped (460 bp) products are shown schematically.

FIGS. 8A-8B show blind comparison of 13 PMO oligonucleotide sequences to skip human exon 53. Myoblasts derived from a DMD patient carrying a deletion of dystrophin exons 45-52 were transfected at 300 nM in duplicate with each of the PMOs by nucleofection. RNA was harvested 3 days following transfection, and amplified by nested RT-PCR. (FIG. 8A) Bars indicate the percentage of exon skipping achieved for each PMO, derived from Image J analysis of the electropherogram of the agarose gel (FIG. 8B). Skipped (477 bp) and unskipped (689 bp) products are shown schematically.

(FIG. 9A) Myoblasts derived from a DMD patient carrying a deletion of dystrophin exons 45-52 were transfected with the six best-performing PMOs by nucleofection, at doses ranging from 25 nM to 400 nM. RT-PCR products derived from RNA isolated from cells 3 days post-transfection were separated by agarose gel electrophoresis. (FIG. 9B) The percentage of exon skipping observed is expressed for each concentration of each PMO as a comparison of the percentage OD of skipped and unskipped band, as measured using Image J.

FIGS. 10A-10E show persistence of dystrophin expression in DMD cells following PMO treatment. (FIG. 10A) Myoblasts derived from a DMD patient carrying a deletion of dystrophin exons 45-52 were transfected by nucleofection at 300 nM with each of the six best-performing PMOs, and were cultured for 1 to 10 days before extracting RNA. The percentage of exon skipping was compared using the percentage OD of skipped and unskipped bands, measured using Image J analysis of the agarose gel of the nested RT-PCR products shown in (FIG. 10A). The experiment was repeated, but this time using the two best-performing PMOs from the previous analysis, and continuing the cultures for 21 days post-transfection (FIGS. 10C and 10D). (FIG. 10E) Western blot analysis was performed on total protein extracts from del 45-52 DMD cells 7 days after transfection with the six best PMOs (300 nM). Blots were probed with antibodies to dystrophin, to dysferlin as a muscle-specific loading control, and protogold for total protein loading control. CHQSB myoblasts, after 7 days of differentiation were used as a positive control for dystrophin protein (normal).

DETAILED DESCRIPTION OF THE INVENTION

Figure 1:
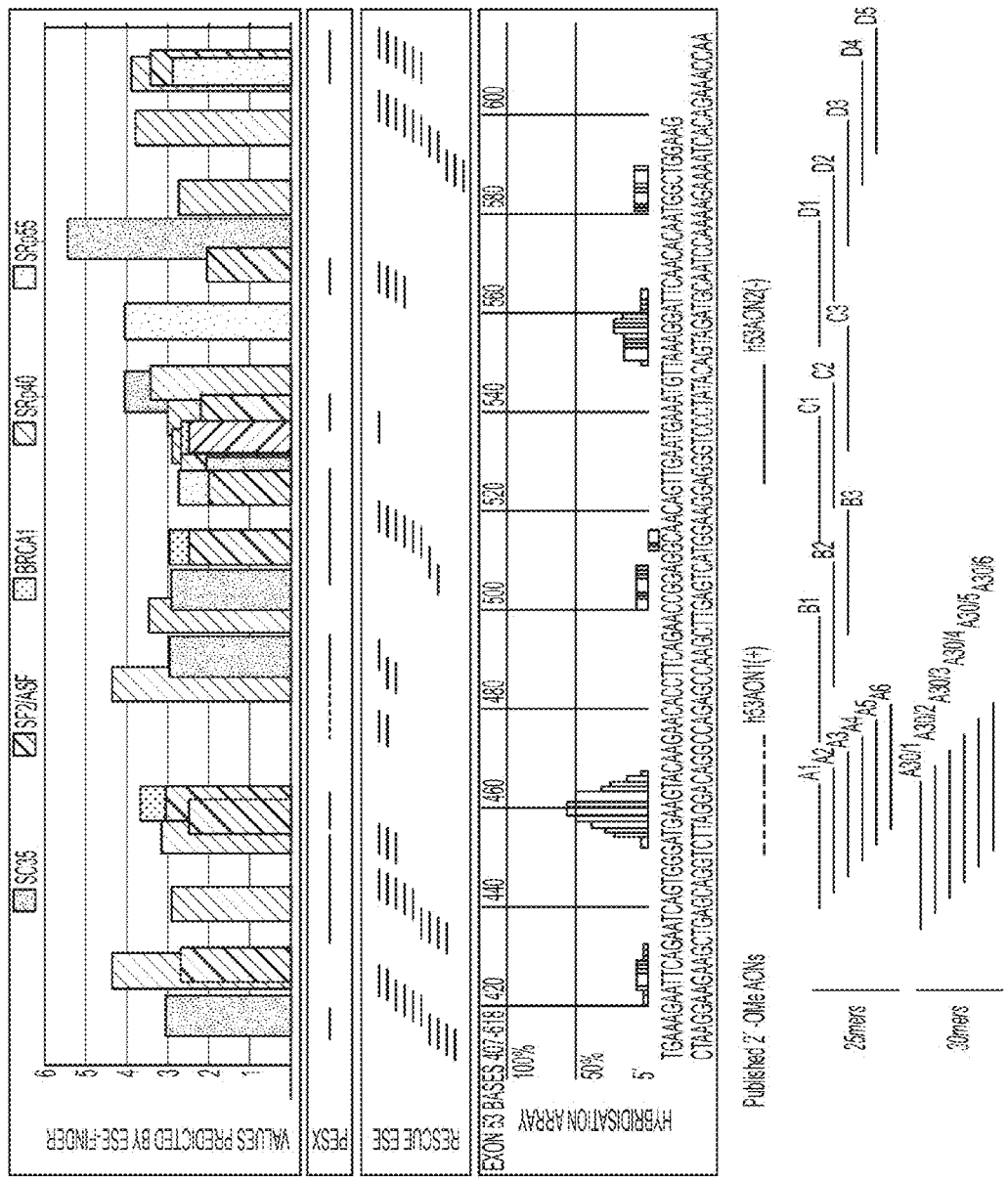
FIGS. 1A-1F show a scheme summarizing the tools used in the design of PMOs to exon 53.

Without being restricted to any particular theory, it is thought by the inventors that the binding of the molecules to the dystrophin pre-mRNA interacts with or interferes with the binding of SR proteins to the exon of interest. SR proteins are involved in the slicing process of adjacent exons. Therefore, it is thought that interacting or interfering with the binding of the SR proteins interferes with the splicing machinery resulting in exon skipping.

The base "X" in the above base sequences is defined as being thymine (T) or uracil (U). The presence of either base in the sequence will still allow the molecule to bind to the pre-mRNA of the dystrophin gene as it is a complementary sequence. Therefore, the presence of either base in the molecule will cause exon skipping. The base sequence of the molecule may contain all thymines, all uracils or a combination of the two. One factor that can determine whether X is T or U is the chemistry used to produce the molecule. For example, if the molecule is a phosphorodiamidate morpholino oligonucleotide (PMO), X will be T as this base is used when producing PMOs. Alternatively, if the molecule is a phosphorothioate-linked 2'-O-methyl oligonucleotide (2'OMePS), X will be U as this base is used when producing 2'OMePSs. Preferably, the base "X" is only thymine (T).

The advantage provided by the molecule is that it causes a high level of exon skipping. Preferably, the molecule causes an exon skipping rate of at least 50%, more preferably, at least 60%, even more preferably, at least 70%, more preferably still, at least 76%, more preferably, at least 80%, even more preferably, at least 85%, more preferably still, at least 90%, and most preferably, at least 95%.

The molecule can be any type of molecule as long as it has the selected base sequence and can bind to a target site of the dystrophin pre-mRNA to cause exon skipping. For example, the molecule can be an oligodeoxyribonucleotide, an oligoribonucleotide, a phosphorodiamidate morpholino oligonucleotide (PMO) or a phosphorothioate-linked 2'-O-methyl oligonucleotide (2'OMePS). Preferably, the oligonucleotide is a PMO. The advantage of a PMO is that it has excellent safety profiles and appears to have longer lasting effects in vivo compared to 2'OMePS oligonucleotides. Preferably, the molecule is isolated so that it is free from other compounds or contaminants.

The base sequence of the molecule can vary from the selected sequence at up to two base positions. If the base sequence does vary at two positions, the molecule will still be able to bind to the dystrophin pre-mRNA to cause exon skipping. Preferably, the base sequence of the molecule varies from the selected sequence at one base position and, more preferably, the base sequence does not vary from the selected sequence. The less that the base sequence of the molecule varies from the selected sequence, the more efficiently it binds to the specific exon region in order to cause exon skipping.

The molecule is at least 25 bases in length. Preferably, the molecule is at least 28 bases in length. Preferably, the molecule is no more than 35 bases in length and, more preferably, no more than 32 bases in length. Preferably, the molecule is between 25 and 35 bases in length, more preferably, the molecule is between 28 and 32 bases in length, even more preferably, the molecule is between 29 and 31 bases in length, and most preferably, the molecule is 30 bases in length. It has been found that a molecule which is 30 bases in length causes efficient exon skipping. If the molecule is longer than 35 bases in length, the specificity of the binding to the specific exon region is reduced. If the molecule is less than 25 bases in length, the exon skipping efficiency is reduced.

The molecule may be conjugated to or complexed with various entities. For example, the molecule may be conjugated to or complexed with a targeting protein in order to target the molecule to muscle tissue. Alternatively, the molecule may be complexed with or conjugated to a drug or another compound for treating DMD. If the molecule is conjugated to an entity, it may be conjugated directly or via a linker. In one embodiment, a plurality of molecules directed to exon skipping in different exons may be conjugated to or complexed with a single entity. Alternatively, a plurality of molecules directed to exon skipping in the same exon may be conjugated to or complexed with a single entity. For example, an arginine-rich cell penetrating peptide (CPP) can be conjugated to or complexed with the molecule. In particular, (R-Ahx-R)(4)AhxB can be used, where Ahx is 6-aminohexanoic acid and B is beta-alanine [35], or alternatively (RXRRBR)2XB can be used [36]. These entities have been complexed to known dystrophin exon-skipping molecules which have shown sustained skipping of dystrophin exons in vitro and in vivo.

In another aspect, the present invention provides a vector for ameliorating DMD, the vector encoding a molecule of the invention, wherein expression of the vector in a human cell causes the molecule to be expressed. For example, it is possible to express antisense sequences in the form of a gene, which can thus be delivered on a vector. One way to do this would be to modify the sequence of a U7 snRNA gene to include an antisense sequence according to the invention. The U7 gene, complete with its own promoter sequences, can be delivered on an adeno-associated virus (AAV) vector, to induce bodywide exon skipping. Similar methods to achieve exon skipping, by using a vector encoding a molecule of the invention, would be apparent to one skilled in the art.

The present invention also provides a pharmaceutical composition for ameliorating DMD, the composition comprising a molecule as described above or a vector as described above and any pharmaceutically acceptable carrier, adjuvant or vehicle.

Pharmaceutical compositions of this invention comprise any molecule of the present invention, and pharmaceutically acceptable salts, esters, salts of such esters, or any other compound which, upon administration to a human, is capable of providing (directly or indirectly) the biologically active molecule thereof, with any pharmaceutically acceptable carrier, adjuvant or vehicle. Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions of this invention may be administered orally, parenterally, by inhalation spray, topically, rectally, nasally, buccally, vaginally, intradermally or via an implanted reservoir. Oral administration or administration by injection is preferred. The pharmaceutical compositions of this invention may contain any conventional non-toxic pharmaceutically-acceptable carriers, adjuvants or vehicles. The term parenteral as used herein includes subcutaneous, intracutaneous, intravenous, intramuscular, intraarticular, intrasynovial, intrasternal, intrathecal, intralesional and intracranial injection or infusion techniques. Preferably, the route of administration is by injection, more preferably, the route of administration is intramuscular, intravenous or subcutaneous injection and most preferably, the route of administration is intravenous or subcutaneous injection.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent, dispersant or similar alcohol.

The pharmaceutical compositions of this invention may be orally administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavouring and/or colouring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

In one embodiment, the pharmaceutical composition may comprise a plurality of molecules of the invention, each molecule directed to exon skipping in a different exon. Alternatively, the pharmaceutical composition may comprise a plurality of molecules of the invention, each molecule directed to exon skipping in the same exon.

In another embodiment, the pharmaceutical composition may comprise a plurality of vectors of the invention, each vector encoding a molecule directed to exon skipping in a different exon. Alternatively, the pharmaceutical composition may comprise a plurality of vectors of the invention, each vector encoding a molecule directed to exon skipping in the same exon.

In yet another embodiment, the pharmaceutical composition may comprise a molecule and a vector, wherein the molecule and the molecule encoded by the vector are directed to exon skipping in the same or different exons.

The present invention also provides a molecule of the invention for use in therapy.

Further, the present invention provides a molecule of the invention for use in the amelioration of DMD.

The molecules of the present invention cause exon skipping in the dystrophin pre-mRNA. This causes a truncated but functional dystrophin protein to be expressed which results in a syndrome similar to Becker muscular dystrophy (BMD). Therefore, the symptoms of DMD will not be completely treated but will be ameliorated so that they are potentially no longer life threatening.

The present invention also provides a method of ameliorating DMD in a human patient, the method comprising administering a therapeutically effective amount of the molecule of the invention to the patient.

The particular molecule that is administered to the patient will depend on the location of the mutation or mutations present in the dystrophin gene of the patient. The majority of patients have deletions of one or more exons of the dystrophin gene. For example, if a patient is missing exon 44, the process of joining exon 43 to exon 45 will destroy the protein, thus causing DMD. If exon 45 is skipped using a molecule of the invention, the joining of exon 43 to exon 46 will restore the protein. Similarly, a patient with a deletion of exon 45 can be treated with a molecule to skip either exon 44 or exon 46. Further, a patient with a deletion of exons 45 to 52 inclusive (a large portion of the gene), would respond to skipping of exon 53.

In another aspect, the invention provides a kit for the amelioration of DMD in a patient, the kit comprising a molecule of the invention and instructions for its use. In one embodiment, the kit may contain a plurality of molecules for use in causing exon skipping in the same exon or a plurality of exons.

EXAMPLES

Example 1

Here, the first detailed study of the role that AO target site variables have on the efficacy of PMOs to induce skipping is reported. The results reported here should have an impact on the initial planning and design of AOs for future potential clinical trials.

Materials and Methods

Hybridization Analyses

Templates for the production of synthetic pre-mRNAs for exons 44, 45, 46, 51, and 53 of the human dystrophin gene (DMD gene) were generated by PCR amplification from genomic clones of the exons, together with approximately 500 nt of upstream and downstream introns. PCR primers incorporated T7 RNA polymerase promoter sequences, such that pre-mRNAs could be produced by in vitro transcription. Pre-mRNAs were then subjected to a hybridization screen against a spotted array of all 4096 possible hexanucleotide sequences (Access Array 4000; Nyrion Ltd, Edinburgh UK). Binding of the pre-mRNA to specific spots on the array was detected by reverse transcriptase-mediated incorporation of biotinylated nucleotides by primer extension, followed by fluorescent labelling. Scanning of the arrays followed by software analysis enabled sequences within the exons that were accessible to binding to the hexamer array to be identified. Using a hybridization assay, binding accessibility of each exons were analysed and hybridization peak identified by AccessMapper software (Nyrion Ltd) (see FIG. 1D).

AO Design

Overlapping AOs were designed to exons 44, 45, 46, 51, and 53 of the human DMD gene using the following information: putative SR protein binding domains as predicted by ESEfinder [20, 21], Rescue ESE [24] and PESX [22, 23] analyses of exon sequence; sequences accessible to binding as determined by hybridization analyses (Nyrion); previously published work [18, 19].

All AOs were synthesized as phosphorodiamidate morpholino oligos (PMOs) by Gene Tools LLC (Philomath Oreg., USA). To facilitate transfection of these uncharged oligonucleotides into cultured cells, the PMOs were hybridized to phosphorothioate-capped oligodeoxynucleotide leashes, as described by Gebski et al., [12], and stored at 4° C.

The sequences of some of these PMOs were as follows:

H44A30/1-
(SEQ ID NO: 13)
TGA AAA CGC CGC CAT TTC TCA ACA GAT CTG;

H44A30/2-
(SEQ ID NO: 14)
CAT AAT GAA AAC GCC GCC ATT TCT CAA CAG;

H44AB30/2-
(SEQ ID NO: 15)
TGT TCA GCT TCT GTT AGC CAC TGA TTA AAT;

H45A30/2-
(SEQ ID NO: 16)
CAG TTT GCC GCT GCC CAA TGC CAT CCT GGA;

H45A30/1-
(SEQ ID NO: 17)
TTG CCG CTG CCC AAT GCC ATC CTG GAG TTC;

H46A30/2-
(SEQ ID NO: 18)
TGC TGC TCT TTT CCA GGT TCA AGT GGG ATA;

H46A30/4-
(SEQ ID NO: 19)
CTT TTA GTT GCT GCT CTT TTC CAG GTT CAA;

H46A30/5-
(SEQ ID NO: 20)
CTT TTC TTT TAG TTG CTG CTC TTT TCC AGG;

H46A30/3-
(SEQ ID NO: 21)
TTA GTT GCT GCT CTT TTC CAG GTT CAA GTG;

H53A30/2-
(SEQ ID NO: 22)
CTG TTG CCT CCG GTT CTG AAG GTG TTC TTG;

H53A30/3-
(SEQ ID NO: 23)
CAA CTG TTG CCT CCG GTT CTG AAG GTG TTC;

H53A30/1-
(SEQ ID NO: 24)
TTG CCT CCG GTT CTG AAG GTG TTC TTG TAC.

Cell Culture and AO Transfection

Normal human primary skeletal muscle cells (TCS Cellworks, Buckingham, UK) were seeded in 6-well plates coated with 0.1 mg/ml ECM Gel (Sigma-Aldrich, Poole, UK), and grown in supplemented muscle cell growth medium (Promocell, Heidelberg, Germany). Cultures were switched to supplemented muscle cell differentiation medium (Promocell) when myoblasts fused to form visible myotubes (elongated cells containing multiple nuclei and myofibrils). Transfection of PMOs was then performed using the transfection reagent Lipofectin (Invitrogen, Paisley, UK) at a ratio of 4 µl of Lipofectin per µg of PMO (with a range of PMO concentrations tested from 50 to 500 nM, equivalent to approximately 0.5 to 5 µg) for 4 hrs, according to the manufacturer's instructions. All transfections were performed in triplicate in at least two different experiments.

RNA Isolation and Reverse Transcriptase-Polymerase Chain Reaction Analysis

Typically 24 h after transfection, RNA was extracted from the cells using the QIAshredder/RNeasy system (Qiagen, Crawley, UK) and ~200 ng RNA subjected to RT-PCR with DMD exon-specific primers using the GeneScript kit (Genesys, Camberley, UK). From this 20 cycle reaction, an aliquot was used as a template for a second nested PCR consisting of 25 cycles. PCR products were analysed on 1.5% agarose gels in Tris-borate/EDTA buffer. Skipping efficiencies were determined by quantification of the PCR products by densitometry using GeneTools software (Syngene, Cambridge, UK).

Statistical Analysis

The non-parametric Mann-Whitney rank sum test was used to identify whether parameters for effective PMOs were significantly different to those for ineffective PMOs. Where data was calculated to fit a normal distribution, the more powerful two-tailed Student's t-test was performed instead. Correlations were generated using the Spearman rank-order test. To determine the strength of the combined significant parameters/design tools to design effective PMOs, linear discriminant analysis was used [34], with the lda function from the MASS package, using "effective" or "ineffective" as the two prior probabilities. The Ida function produces posterior probabilities for the two classes (effective and ineffective) for each PMO by leave-one-out classification.

Results

PMO Design and Analysis of Bioactivity

A unique set of 66 PMOs has been designed to target exons 44, 45, 46, 51, and 53 of the human gene for dystrophin. The design process for exon 53 is depicted in FIGS. 1A-1F, and has also been performed for the other four exons (data not shown). The exon sequence was analysed for the presence of exonic splicing enhancers (ESE) and exonic splicing suppressors or silencers (ES S) and the outputs aligned for the three available algorithms, ESEfinder (FIG. 1A) [20, 21], PESX (FIG. 1B) [22, 23], and Rescue ESE (FIG. 1C) [24]. Hybridization array analysis was also performed for each exon in vitro, as described in Materials and Methods. The peaks shown in FIG. 1D indicate areas of the exon that are in a conformation able to hybridize to the array, and which may consequently prove more accessible to antisense AOs. The coincidence of ESEs, as predicted by two or more algorithms, and hybridization peaks determined experimentally, was used to design arrays of 25 mer and, subsequently, 30 mer PMOs, the positions of which are shown in FIG. 1F. The binding sites for 2'OMePS AOs described previously [18] are shown for comparison (see FIG. 1E).

Figure 2:
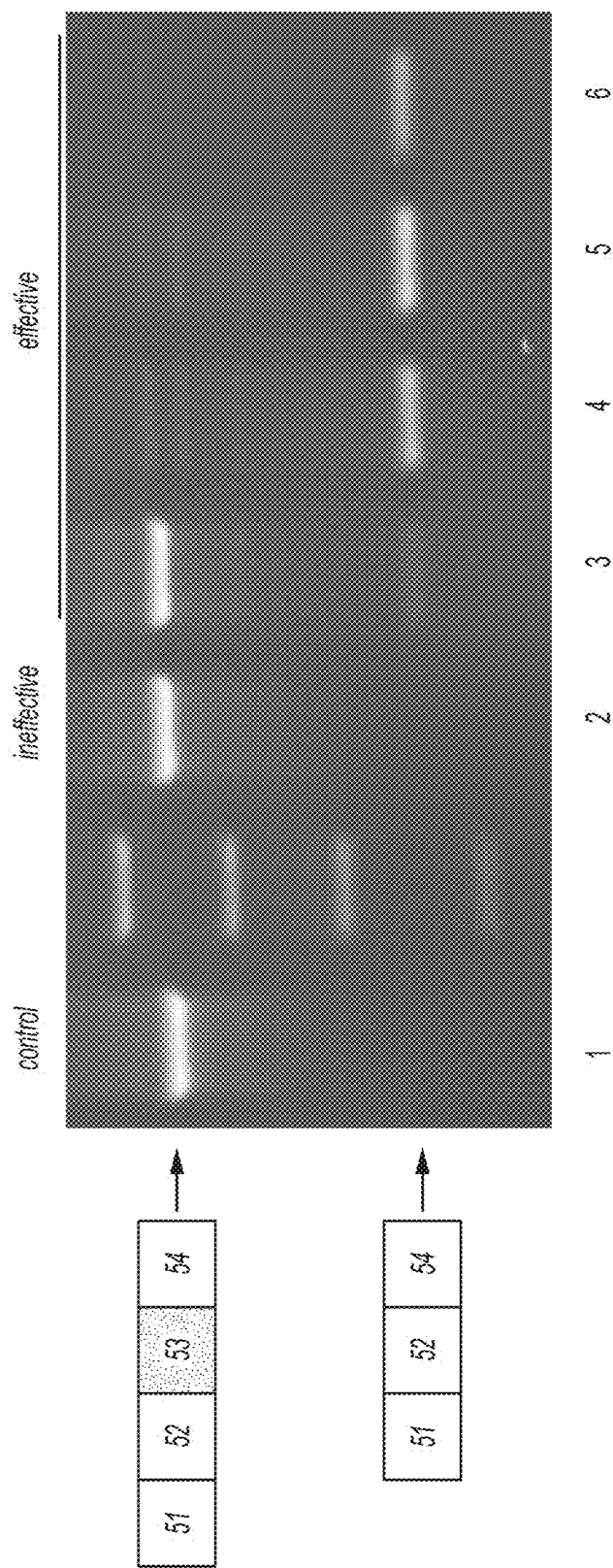
FIG. 2 shows a comparison of active (effective) and inactive (ineffective) PMOs. RT-PCR analysis of mRNA from normal human skeletal muscle cells treated with PMOs to exon 53 demonstrates a wide variation in the efficiency of exon skipping. Over 75% exon skipping is seen with h53A30/2 (lane 5) and h53A30/3 (lane 6). h53A30/1 (lane 4) produced around 50% skipping, while the 25-mer h53A1 (lane 3) produced just over 10% skipping. In contrast, h53C1 (lane 2) was completely inactive. Lane 1 contains a negative control in which cells were treated with lipofectin but no PMO.

Each PMO was tested in primary cultures of human skeletal muscle, in triplicate, in at least two experiments, and over a range of concentrations from 50 nM to 500 nM. Their bioactivity was determined by RT-PCR analysis, which showed a wide variation in the level of exon skipping induced (FIG. 2, and data not shown), ranging from 0% for h53C1 (FIG. 1F and FIG. 2, lane 2) to 80% for h53A30/3 (FIG. 1F and FIG. 2, lane 6). Sequencing of the PCR products verified accurate skipping of the targeted exon (data not shown). The activity of each PMO at the stated optimal concentration is summarized in Table 1. Bioactivity is expressed as a percentage of the skipped amplicon relative to total PCR product, as assessed by densitometry. Specific, consistent and sustained exon skipping was evident for 44 of the 66 PMOs tested.

In Silico Analysis of PMOs

Figure 3:
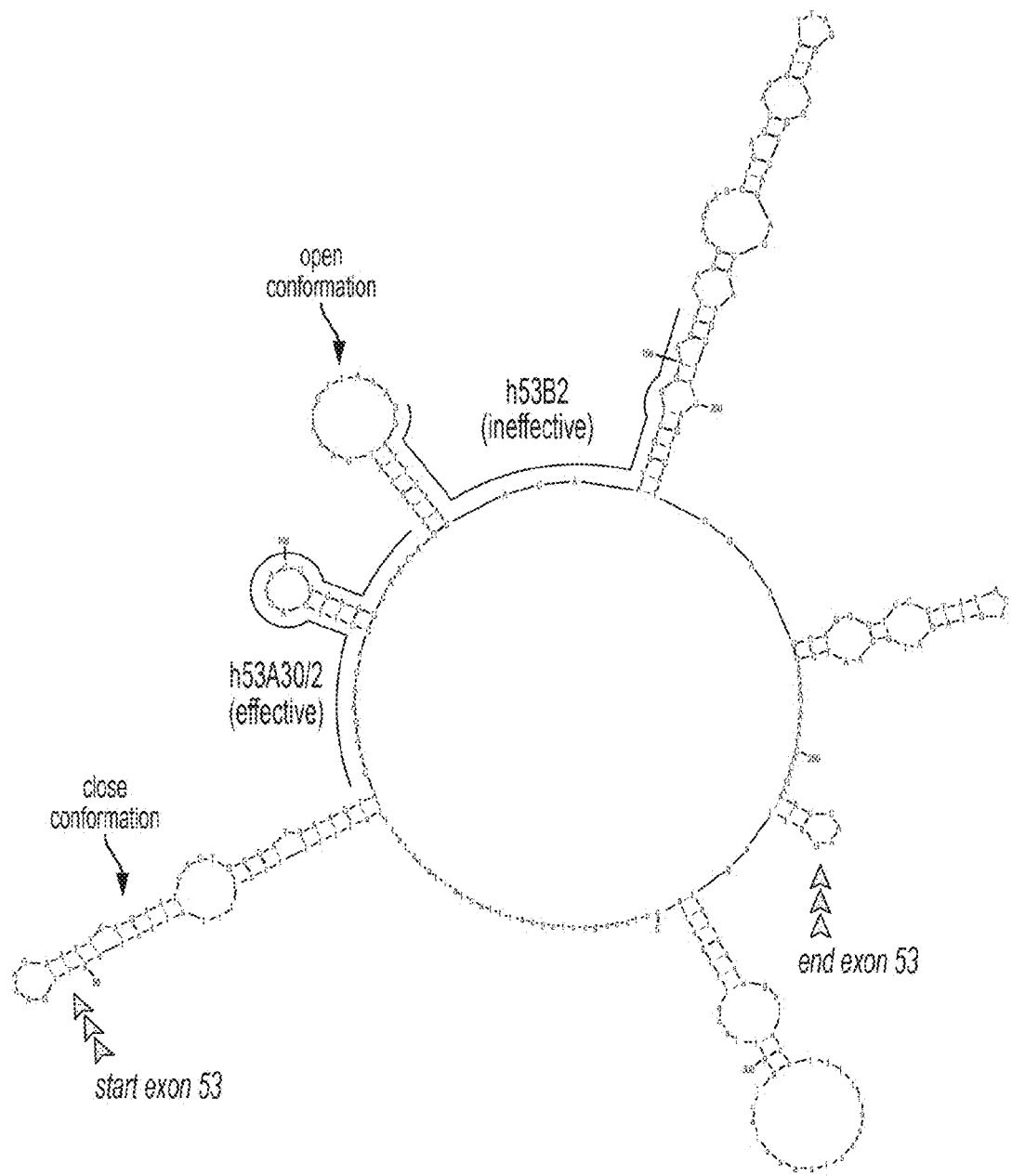
FIG. 3 shows an Mfold secondary structure prediction for exon 53 of the human dystrophin gene. MFOLD analysis [25] was performed using exon 53 plus 50 nt of the upstream and downstream introns, and with a maximum base-pairing distance of 100 nt. The intron and exon boundaries are indicated, as are the positions of the target sites of the bioactive PMO h53A30/2 (87.2% skip) and an inactive PMO (h53B2). Examples of open and closed RNA secondary structure are arrowed.
Figure 4A:
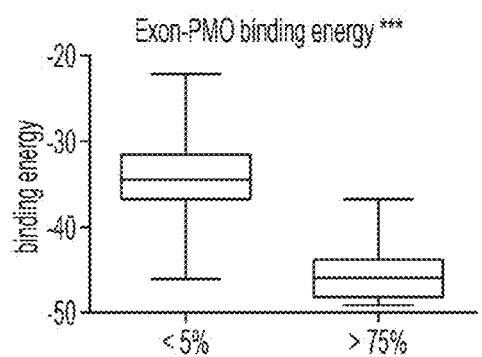
FIGS. 4A-4D show boxplots of parameters significant to strong PMO bioactivity. Comparisons were made between inactive PMOs and those inducing skipping at levels in excess of 75%. Boxplots are shown for parameters which are significant on a Mann-Whitney rank sum test: PMO to target binding energy (FIG. 4A), distance of the target site from the splice acceptor site (FIG. 4B), the percentage overlap with areas of open conformation (FIG. 4C), as predicted by MFOLD software, and the percentage overlap of the target site with the strongest area accessible to binding (FIG. 4D), as revealed by hexamer hybridization array analysis. Degrees of significance are indicated by asterisks. *: $p<0.05$; : $p<0.01$; *: $p<0.001$.
Figure 4B:
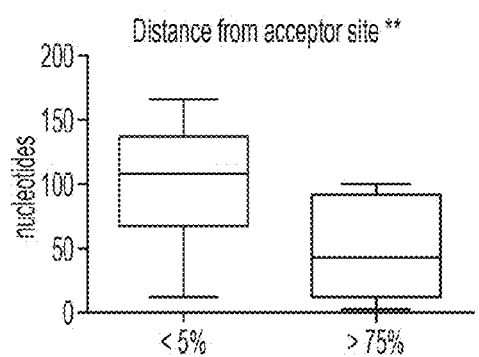
Figure 4C:
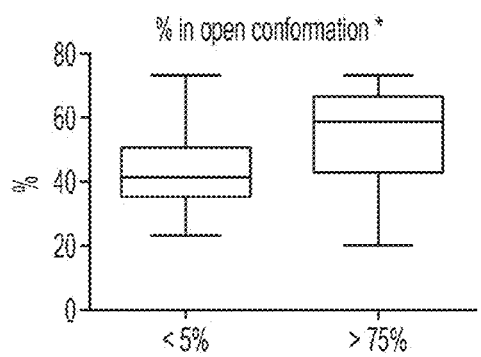
Figure 4D:
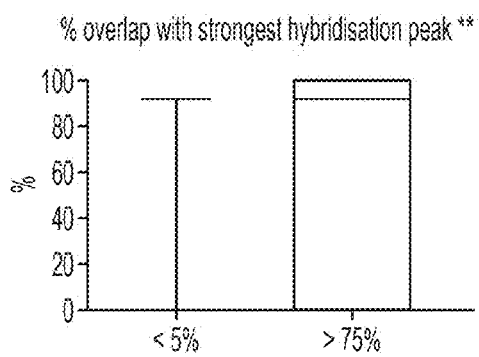
Figure 5A:
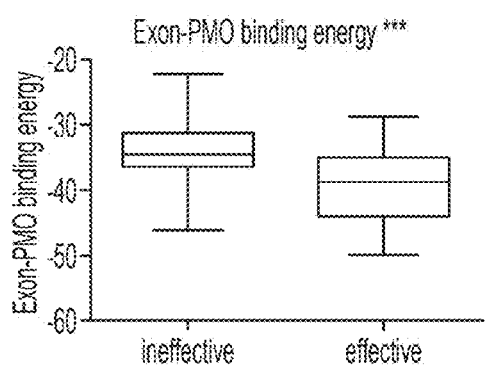
FIGS. 5A-5D show boxplots of parameters significantly different between bioactive (effective) and inactive (ineffective) PMOs. Comparisons were made between PMOs determined as bioactive (those that induced skipping at greater than 5%) and those that were not. Boxplots are shown for parameters which are significant from a Mann-Whitney rank sum test: PMO to target binding energy (FIG. 5A), distance of the target site from the splice acceptor site (FIG. 5B), the score over threshold for a predicted binding site for the SR protein SF2/ASF (FIG. 5C), and the percentage overlap of the target site with the strongest area accessible to binding (FIG. 5D), as revealed by hexamer hybridization array analysis. Degrees of significance are indicated by asterisks. *: $p<0.05$; : $p<0.01$; *: $p<0.001$.
Figure 5B:
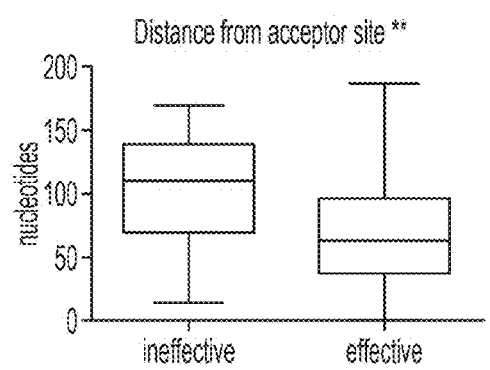
Figure 5C:
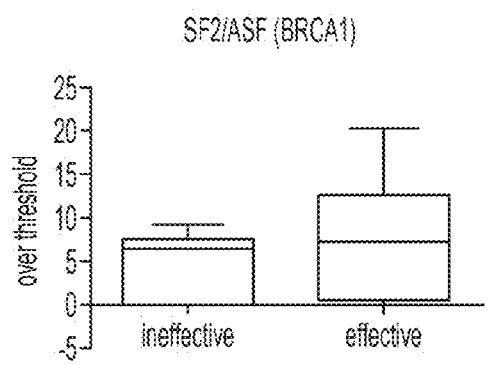
Figure 5D:
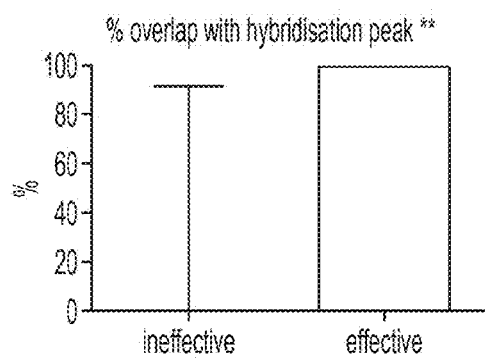

We then performed a retrospective in silico analysis of the characteristics of all 66 PMOs tested in this study, with respect to PMO length, the distance of the PMO target site from the splice donor and acceptor sites, PMO-to-target binding energy and PMO-to-PMO binding energy, as calculated using RNAstructure 2.2 software for the equivalent RNA-RNA interaction, and percentage GC content of the PMO, the results of which are summarized in Table 1. Also shown in Table 1 is the percentage overlap of each PMO target site with sequences shown to be accessible to binding, as determined experimentally by the hexamer hybridization array analysis. The relationship of PMO target site and RNA secondary structure was also examined using the program MFOLD [25] (FIG. 3 and data not shown), with the percentage overlap of PMO target site with sequence predicted to be in open conformation by MFOLD analysis given in Table 1. ESEfinder and SSF (accessible on the world-wide web at umd.be/SSF/) software analysis of exon sequences revealed the positions of putative SR protein binding motifs (SF2/ASF (by two algorithms), SC35, SRp40, SRp55, Tra2β and 9G8). The highest score over threshold for each SR protein is given for each PMO in the columns on the right of Table 1. Also shown is the degree of overlap of each PMO target site with the ESE and ESS regions predicted by Rescue ESE and PESX.

Statistical Analysis of Design Parameters in Relation to PMO Bioactivity

For this statistical analysis, bioactive PMOs are considered to be those which produce over 5% skipping, while those that produce less than 5% skipping are considered inactive. For each of the parameters listed in Table 1, comparison was made between bioactive and inactive PMOs using the non-parametric Mann-Whitney rank sum test, or, when it was statistically valid to do so, the parametric Student's t-test (two-tailed). The significant parameters are listed in Table 2. Considering the data as a whole, the variable which showed the highest significance to PMO bioactivity was the binding energy of the PMO to the exon ($p=0.001$); the most bioactive exons are predicted to bind better to their target sites. Those PMOs that overlap with peaks identified by the experimental hybridization array analysis are not significantly more active than those that do not ($p=0.056$), but when only the strongest peak for each exon is considered, this parameter becomes highly significant ($p=0.003$). Distance of the PMO target site to the splice acceptor site of the exon was also highly significant ($p=0.004$), with PMOs whose target site were closer to the acceptor site being more active. PMOs whose target sites showed coincidence with binding motifs for the SR protein SF2/ASF (as defined by the BRCA1 algorithm of Smith et al. [21]) produced significantly greater skipping ($p=0.026$). PMO length is also a significant parameter ($p=0.017$), with longer PMOs being more effective at inducing skipping. Boxplots of the significant variables identified here are shown in FIGS. 5A-5D. None of the other variables considered in this study were shown to have any significance to AO bioactivity.

To ascertain which parameters/design tools are the most powerful, we also used the Mann-Whitney rank sum test to compare the most active PMOs (i.e. those that induce greater than 75% skipping of the target exon) to those that were inactive (i.e. those that produce less than 5% skipping). Boxplots of the significant variables for this comparison are shown in FIGS. 4A-4D. There is strong significance of overlap of the PMO target site with the strongest hybridization peak for each exon ($p=0.002$); more of the most bioactive PMOs had their target sites coincident with sequences accessible to binding than those that were inactive. This is reinforced by the observation that the target sites of PMOs that produced over 75% skipping significantly overlapped more RNA that was in open conformation, relative to inactive PMOs ($p=0.025$). Stronger binding between the PMO and its target exon, PMO length, and proximity of the target to the acceptor site are also significant parameters when comparing the most and least effective reagents.

Spearman's rank order correlation was used to establish potential relationships between design parameters and skipping bioactivity using the entire set of PMOs. This shows a strong correlation between skipping bioactivity and PMO-target binding energy ($r_s=-0.618$, $p=0$), percentage open conformation ($r_s=0.275$, $p=0.0259$), PMO length ($r_s=0.545$, $p=0$), distance from the splice acceptor site ($r_s=-0.421$, $p=0$), percentage overlap with the strongest hybridization peak ($r_s=0.46$, $p=0$), and overlap with an ESS sequence, as predicted by PESX ($r_s=0.261$, $p=0.0348$).

Linear Discriminant Analysis

This analysis was performed on all possible combinations of length, overlap with the SF2/ASF (BRCA1) motif, percentage overlap with areas of open conformation, percentage overlap with hybridization peak and PMO-target binding energy, i.e. PMO parameters and design tools that showed significance or borderline significance. Using length, SF2/ASF (BRCA1) motif and hybridization peak data, nine of the inactive PMOs were classified as bioactive and four bioactive PMOs were classified as inactive (Table 3). These four misclassified PMOs were 25 mers to exon 46, three of which have borderline bioactivity, i.e. produce just 10% skipping, while the fourth produces about 20% skipping. Taken overall, this equates to 80% of the PMOs being predicted correctly when assessed according to their length, SF2/ASF (BRCA1) overlap and hybridization peak overlap. This would suggest that these parameters have the potential to be effective design tools, with four out of every five PMOs designed to have these three properties likely to be bioactive. In line with this, there was a distinct trend for PMOs being correctly assigned as bioactive with increased skipping bioactivity (see Table 3). Indeed, the PMOs with greatest bioactivity were all 30 mers (10/10), bound to their target with a high binding energy of below −43.0 kD (9/10), overlapped by over 50% with areas of open conformation (7/10), overlapped with SF2/ASF (BRCA1) peak (8/10), and overlapped with a hybridization peak (7/10).

Discussion

Clinical studies using AOs to skip exon 51 to correct DMD deletions are progressing well [11; F. Muntoni, Principal Investigator of MDEX Consortium, personal communication]. However since the mutations that cause DMD are so diverse, skipping of exon 51 would have the potential to treat just 24.6% of DMD patients on the Leiden DMD database [26]. It is therefore imperative that pre-clinical optimization of AO target sequence and chemistry is continually studied and improved. This study has examined the significance of design parameters for PMO-induced skipping of exons 44, 45, 46, 51, and 53, which would have the potential to treat, respectively, 11.5%, 15.8%, 8.4%, 24.6% and 13.5% of DMD patients in the Leiden database [26; A. Aartsma-Rus, personal communication].

Specific skipping was observed for the five DMD exons studied here, with two-thirds of the PMOs tested being bioactive. This proportion of bioactive AOs within a cohort has been reported previously [18, 19], but we have induced high-level (i.e. greater than 75%) skipping in four of the five exons tested, some of which are achievable at relatively low doses of oligomer. The exception is exon 51, published previously [4], achieving a maximal skipping of 26%. The work of Wilton et al [19] demonstrated that only exons 51 and 53 can be skipped with high efficiency (>30% by their definition), and that exons 44, 45 and 46 are less "skippable" (less than 30% skipping). Furthermore, Aartsma-Rus et al [18] showed oligomers capable of high-level skipping (greater than a mere 25%) for only exons 44, 46 and 51.

We provide here direct evidence that AO bioactivity shows a significant association with accessibility of its target site to binding. This is the first study to assess sequences practically within the pre-mRNA that are accessible to binding and then use them as an aid to AO design. The data we show underline the value of the hybridization analysis in determining what are likely to be the most bioactive oligomers (i.e. those that produce greater than 75% skipping). As an example, if we look at the data for oligomers developed for exon 45 [18], we see that there is only one moderately effective (5-25%) reagent for this otherwise unskippable exon. This oligomer is the only one of the six tested that overlaps with the strongest peak in our hybridization analysis. The partial nature of this overlap, combined with the short length of the oligomer, is likely to contribute to its relative weakness compared to the PMOs we have developed here. In general, the 2'OMePS AOs displaying the highest bioactivity in the work of Aartsma-Rus et al. [18] and Wilton et al. [19], show some degree of overlap with the hybridization peaks that we have defined here for exons 45, 46 and 53.

Ease of skipping of certain DMD exons has been seen elsewhere [18] and may be related to other factors affecting splicing, including strength of splice donor and acceptor sites and branchpoint, and the size of upstream and downstream introns, which may affect the order in which exons are spliced together. There is the potential of using a cocktail of AOs to induce greater skipping of the more difficult to skip exons [27, 28].

Accessibility of the AO to its target site depends directly on the secondary structure of the pre-mRNA, which has a major role in determining AO bioactivity in cells. A study in which the structure around an AO target site was changed revealed that AOs were unable to invade very stable stem-loop structures and their antisense activity was inhibited, but generally showed good activity when impeded by little local structure [29]. Overlap of PMO target sites with open conformations in the folded RNA showed a weak association with PMO bioactivity, which was more obvious when only the stronger PMOs were considered in the statistical analysis. It is also possible that there is selective pressure for SR binding sites to be located preferentially on these open secondary structures. The presumption is that binding of bioactive PMOs to their target sites sterically block the binding of important factors involved in RNA processing, resulting in exon skipping.

One of the PMO parameters with high significance was length; 30 mer PMOs were far superior to their 25 mer counterparts. The influence of 2'OMePS AO length on bioactivity has been reported elsewhere [30] and such an observation for PMO-induced skipping of exon 51 has been reported previously by us [4]. The more persistent action of longer PMOs would have important cost and dose implications in the choice of AO for clinical trials. Longer AOs are likely to sterically block more of the regions that interact with the splicing machinery, but in general terms, the energy of binding of the longer PMO to its target would be increased, which we showed to be the most significant parameter in AO design. The strong significance of the binding energy of PMO-target complexes (i.e., free energy of AO-target compared to free energy of the target) and PMO length to bioactivity suggests that PMO bioactivity depends on stability of the PMO-target complex, and implies that bioactive PMOs act by interference of target RNA folding. Computational analysis revealed that the thermodynamics of binding of active PMOs to their target site had a dramatic effect on the secondary folded structure of the RNA (data not shown). It is likely that these changes in secondary structure would have a profound effect on the binding of SR proteins to the RNA, thereby disrupting splicing, and exon skipping would ensue.

Overlap of a PMO target site with a binding site motif for the SR protein SF2/ASF (BRCA1), as predicted by ESEfinder, showed a significant association to PMO bioactivity. This partly confirms the work of Aartsma-Rus et al. [18], who observed marginally significantly higher ESEfinder values for SF2/ASF and SC35 motifs for effective AOs when compared to inactive AOs. SC35 and SF2/ASF motifs are the two most abundant proteins assessed by ESEfinder. The reason why we do not see any significance of overlap with SC35 motif to PMO bioactivity may be due to the difference in AO chemistry used, and the number of AOs assessed. However Aartsma-Rus et al. [18] did note that not every bioactive AO has a high value for any of the SR protein binding motifs, and some inactive AOs have high values. The apparent weakness and unreliability of SR protein binding motifs as design tools for AOs may be a reflection of the lack of precision of the predictive software used. Overlap of PMO target site with exonic splicing silencers appears to show a correlation with bioactivity in Spearman's rank order test analysis. Such a correlation would be counter-intuitive and the true significance questionable. Again the strength of the predictive software used may be in doubt. It should be noted that the software programmes used predict SR binding motifs on the linear exon sequence. The availability of these predicted motifs to bind SR proteins, or for binding PMOs to disrupt the binding of these proteins, is directly related to the folding of the pre-mRNA. The discrepancy in the relative significance of secondary RNA structure and SR protein binding motifs may be due to active PMOs disrupting SR protein binding, not sterically but indirectly, by altering the secondary pre-mRNA structure. A very recent study has shown the importance of co-transcriptional pre-mRNA folding in determining the accessibility of AO target sites and their effective bioactivity, and showed a direct correlation between AO bioactivity and potential interaction with pre-mRNA [31].

It has been previously reported that ESE sites located within 70 nucleotides of a splice site are more active than ESE sites beyond this distance [32]. Our results partially support this; PMOs with their target site closer to the splice acceptor site are significantly more bioactive. However distance of the PMO target site to the splice donor site showed no statistical significance to bioactivity. This bias has been previously reported for the analyses of 2'OMePS AOs [18, 19], and may be related to the demonstration, by Patzel et al. [33], of the importance of an unstructured 5' end of RNA in the initiation of hybridization of oligonucleotide binding. This would suggest that targeting any significant parameters located in the 5' part of an exon may increase the probability of designing a bioactive AO.

In conclusion, our findings show that no single design tool is likely to be sufficient in isolation to allow the design of a bioactive AO, and empirical analysis is still required. However this study has highlighted the potential of using a combination of significant PMO parameters/design tools as a powerful aid in the design of bioactive PMOs. Linear discriminant analysis revealed that using the parameters of PMO length, overlap with SF2/ASF (BRCA1) motif and hexamer array hybridization data in combination would have an 80% chance of designing a bioactive PMO, which is an exciting and surprising finding, and should be exploited in further studies.

TABLE 1

Table 1: Table summarizing the characteristics of PMOs used PMOs are ranked in order of efficacy and characteristics of the PMOs and their target sites listed.

| PMO | Targeted exon | Optimal conc. | % Skip[a] | Length | % GC | Exon-PMO binding energy | PMO-PMO binding energy | % open[b] | Ends in open loops[b] | Distance from donor | Distance from accepted | % overlap with hybrid peak |
|---|---|---|---|---|---|---|---|---|---|---|---|---|
| h53B1 | 53 | 500 | 0 | 25 | 28 | −22.1 | −12.1 | 53.3 | 1 | 119 | 68 | 0 |
| h53C1 | 53 | 500 | 0 | 25 | 48 | −32.4 | −9.8 | 46.7 | 2 | 79 | 108 | 0 |
| h53C2 | 53 | 500 | 0 | 25 | 56 | −31.3 | −12.7 | 33.3 | 1 | 72 | 115 | 0 |
| h53C3 | 53 | 500 | 0 | 25 | 60 | −34.6 | −13.7 | 26.7 | 1 | 60 | 127 | 0 |
| h53D1 | 53 | 500 | 0 | 25 | 52 | −34.1 | −13.4 | 30 | 1 | 39 | 148 | 0 |
| h45A30/4 | 45 | 500 | 0 | 30 | 43 | −35.2 | −7.5 | 40 | 1 | 53 | 93 | 100 |
| h45A30/6 | 45 | 500 | 0 | 30 | 53 | −42.4 | −26.9 | 46.7 | 2 | 9 | 137 | 100 |
| h46A10 | 46 | 500 | 0 | 25 | 40 | −35.3 | −1.7 | 23.3 | 1 | 63 | 60 | 0 |
| h46A30/6 | 53 | 500 | 0 | 30 | 40 | −42.1 | −10.1 | 56.7 | 0 | 5 | 113 | 0 |
| h53D2 | 46 | 500 | 0.1 | 25 | 48 | −36.5 | −14.5 | 40 | 2 | 30 | 157 | 0 |
| h46A5 | 53 | 500 | 0.2 | 25 | 36 | −33.9 | −7.9 | 53.3 | 0 | 10 | 113 | 0 |
| h53A6 | 53 | 500 | 0.3 | 25 | 48 | −35.3 | −8.5 | 43.3 | 2 | 138 | 49 | 92 |
| h53B2 | 53 | 500 | 0.6 | 25 | 48 | −30.1 | −11.3 | 23.3 | 1 | 108 | 79 | 0 |
| h46A11 | 46 | 500 | 0.6 | 25 | 20 | −24.5 | −1.5 | 43.3 | 0 | 0 | 143 | 0 |
| h46A30/8 | 46 | 500 | 1.5 | 30 | 30 | −34.2 | −1.8 | 46.7 | 0 | 0 | 136 | 0 |
| h45A30/7 | 45 | 500 | 1.6 | 30 | 50 | −46.1 | −4.7 | 73.3 | 0 | 0 | 158 | 100 |
| h45A30/8 | 45 | 500 | 1.6 | 30 | 40 | −39.3 | −13.7 | 53.3 | 1 | 76 | 70 | 100 |
| h53A3 | 53 | 500 | 2 | 25 | 56 | −36.7 | −13.7 | 36.7 | 0 | 147 | 40 | 0 |
| h46A9 | 46 | 500 | 2.1 | 25 | 28 | −31.5 | −7.6 | 36.7 | 1 | 109 | 14 | 0 |
| h53B3 | 53 | 500 | 3 | 25 | 48 | −34.5 | −5.5 | 48 | 2 | 98 | 89 | 0 |
| h53D3 | 53 | 500 | 3.7 | 25 | 36 | −34.3 | −11.2 | 40 | 1 | 18 | 169 | 0 |
| h44B30/8 | 44 | 500 | 4.6 | 30 | 37 | −28.3 | −23.5 | 40 | 1 | 34 | 84 | 0 |
| h44B30/4 | 44 | 50 | 5 | 30 | 43 | −38.2 | −14.6 | 40 | 0 | 54 | 64 | 0 |
| h46A6 | 46 | 100 | 5.4 | 25 | 36 | −31.5 | −8 | 46.7 | 1 | 0 | 123 | 0 |
| h46A8 | 46 | 500 | 5.4 | 25 | 32 | −28.6 | 0 | 20 | 1 | 76 | 47 | 0 |
| h45A30/3 | 45 | 500 | 6.3 | 30 | 40 | −35.5 | −11.8 | 60 | 1 | 108 | 38 | 100 |
| h53D5 | 53 | 500 | 7.9 | 25 | 36 | −31.5 | −3.3 | 66.7 | 1 | 0 | 187 | 0 |
| h46A1 | 46 | 100 | 8.3 | 25 | 48 | −35.7 | −11.9 | 53.3 | 1 | 38 | 85 | 100 |
| h53A5 | 53 | 250 | 9 | 25 | 48 | −35.5 | −8.5 | 43.3 | 2 | 141 | 46 | 100 |
| h46A7 | 46 | 500 | 9.1 | 25 | 32 | −34.8 | −5.6 | 36.7 | 1 | 123 | 0 | 0 |
| h53A30/5 | 53 | 100 | 9.4 | 30 | 47 | −42.4 | −11.3 | 46.7 | 1 | 141 | 41 | 100 |
| h53A2 | 53 | 100 | 9.7 | 25 | 56 | −36.1 | −17.4 | 46.7 | 1 | 150 | 37 | 100 |
| h53A4 | 53 | 500 | 10.5 | 25 | 48 | −34.3 | −8.5 | 20 | 0 | 144 | 43 | 100 |
| h45A30/5 | 45 | 500 | 11.2 | 30 | 63 | −44 | −21.1 | 26.7 | 0 | 17 | 129 | 100 |
| h53D4 | 53 | 500 | 12.3 | 25 | 32 | −30.9 | −9.2 | 63.3 | 1 | 6 | 181 | 0 |

TABLE 1-continued

Table 1: Table summarizing the characteristics of PMOs used
PMOs are ranked in order of efficacy and characteristics of the PMOs and their target sites listed.

| PMO | | | | | | | | | | | |
|---|---|---|---|---|---|---|---|---|---|---|---|
| h53A1 | 53 | 100 | 12.7 | 25 | 52 | −38.6 | −17.4 | 50 | 2 | 153 | 34 | 92 |
| A25 | 51 | 250 | 14.9 | 25 | 36 | −29.3 | −11.6 | 66.7 | 2 | 146 | 62 | 0 |
| h46A2 | 46 | 500 | 15.6 | 25 | 44 | −31.2 | −10.6 | 56.7 | 1 | 33 | 90 | 100 |
| h46A30/7 | 46 | 500 | 18.5 | 30 | 30 | −34.2 | −6.2 | 53.3 | 1 | 0 | 141 | 0 |
| h46A4 | 46 | 100 | 21.2 | 25 | 44 | −39.9 | −6.3 | 56.7 | 2 | 20 | 103 | 46 |
| h44C30/2 | 44 | 50 | 22 | 30 | 33 | −38 | −7.4 | 36.7 | 1 | 7 | 111 | 0 |
| h44B30/7 | 44 | 100 | 26 | 30 | 37 | −33.9 | −10.9 | 26.7 | 1 | 39 | 79 | 0 |
| h51A | 51 | 500 | 26.3 | 30 | 43 | −40.3 | −15 | 70 | 1 | 137 | 65 | 0 |
| h44B30/6 | 44 | 500 | 32.5 | 30 | 37 | −34.6 | −9.6 | 30 | 2 | 44 | 74 | 0 |
| h44C30/3 | 44 | 500 | 35 | 30 | 33 | −38.9 | −13.8 | 30 | 1 | 2 | 116 | 0 |
| h44B30/1 | 44 | 100 | 35 | 30 | 33 | −35.2 | −7.1 | 66.7 | 1 | 69 | 49 | 0 |
| h53A30/6 | 53 | 500 | 35.9 | 30 | 47 | −42.3 | −8.5 | 56.7 | 1 | 138 | 44 | 100 |
| h53A30/4 | 53 | 100 | 38.6 | 30 | 50 | −43.4 | −17.4 | 43.3 | 1 | 144 | 38 | 100 |
| h44C30/1 | 44 | 100 | 42 | 30 | 37 | −41.1 | −10.4 | 50 | 1 | 12 | 106 | 0 |
| h46A3 | 46 | 100 | 49.7 | 25 | 48 | −43.1 | −5.2 | 56.7 | 2 | 28 | 95 | 100 |
| h44A30/3 | 44 | 250 | 52.1 | 30 | 37 | −42.5 | −8.6 | 56.7 | 1 | 99 | 19 | 0 |
| h53A30/1 | 53 | 100 | 52.4 | 30 | 50 | −48.1 | −17.4 | 56.7 | 1 | 153 | 29 | 92 |
| h44B30/3 | 44 | 500 | 61 | 30 | 43 | −35.4 | −11.4 | 30 | 0 | 59 | 59 | 0 |
| h44B30/5 | 44 | 500 | 63.3 | 30 | 40 | −35.9 | −14.6 | 30 | 1 | 49 | 69 | 0 |
| h45A30/1 | 45 | 500 | 64.5 | 30 | 60 | −49.7 | −11 | 36.7 | 1 | 146 | 0 | 100 |
| h46A30/3 | 46 | 500 | 74.6 | 30 | 43 | −49.8 | −6.3 | 73.3 | 2 | 23 | 95 | 100 |
| h46A30/1 | 46 | 500 | 75.6 | 30 | 47 | −43.5 | −12.3 | 63.3 | 0 | 33 | 85 | 100 |
| h46A30/5 | 46 | 500 | 76.7 | 30 | 40 | −49.2 | −6.3 | 70 | 1 | 15 | 103 | 46 |
| h53A30/3 | 53 | 100 | 80.1 | 30 | 53 | −44.6 | −17.4 | 53.3 | 1 | 147 | 35 | 100 |
| h44B30/2 | 44 | 500 | 80.5 | 30 | 37 | −36.9 | −10.7 | 50 | 1 | 64 | 54 | 0 |
| h53A30/2 | 53 | 100 | 87.2 | 30 | 53 | −45.1 | −17.4 | 63.3 | 1 | 150 | 32 | 100 |
| h46A30/4 | 46 | 500 | 87.3 | 30 | 40 | −47.5 | −6.3 | 73.3 | 2 | 20 | 98 | 85 |
| h46A30/2 | 46 | 500 | 87.9 | 30 | 47 | −49.1 | −13.4 | 63.3 | 2 | 28 | 90 | 100 |
| h45A30/2 | 45 | 500 | 91.4 | 30 | 60 | −46.6 | −13 | 20 | 1 | 142 | 4 | 100 |
| h44A30/2 | 44 | 500 | 95 | 30 | 43 | −44 | −8.6 | 40 | 0 | 104 | 14 | 0 |
| h44A30/1 | 44 | 250 | 97 | 30 | 47 | −47.5 | −11.2 | 46.7 | 1 | 109 | 9 | 0 |

| PMO | # Rescue ESE sites | % overlap with Rescue ESE | % overlap with PESE | % overlap with PESS | ESE finder values over threshold[c] SF2/ASF | BRCA1 | SC35 | SRp40 | SRp55 | Tra2β | 9G8 |
|---|---|---|---|---|---|---|---|---|---|---|---|
| h53B1 | 5 | 56 | 40 | 40 | 0 | 9.26 | 3.62 | 10.66 | 0 | 5.06 | 1.1 |
| h53C1 | 6 | 52 | 72 | 0 | 4.19 | 6.72 | 0 | 2.04 | 0 | 24.04 | 28.68 |
| h53C2 | 1 | 24 | 60 | 0 | 4.19 | 6.72 | 10.2 | 4.38 | 0 | 0 | 8.28 |
| h53C3 | 1 | 24 | 32 | 0 | 3.49 | 6.41 | 10.2 | 4.38 | 6.86 | 0 | 14.18 |
| h53D1 | 4 | 40 | 32 | 0 | 0.52 | 0 | 18.68 | 0 | 6.86 | 0 | 12.71 |
| h45A30/4 | 4 | 40 | 0 | 0 | 6.29 | 4.8 | 5.9 | 17.91 | 0 | 18.18 | 8.14 |
| h45A30/6 | 4 | 40 | 0 | 0 | 11.64 | 7.34 | 5.04 | 1.38 | 0 | 7.25 | 16.53 |
| h46A10 | 7 | 60 | 48 | 8 | 2.21 | 0 | 2.7 | 2.88 | 0 | 5.11 | 23.85 |
| h46A30/6 | 7 | 40 | 50 | 0 | 0 | 0 | 0 | 5.09 | 0 | 24.04 | 6.94 |
| h53D2 | 6 | 44 | 32 | 0 | 0.52 | 1.8 | 18.68 | 0.42 | 0 | 0 | 12.71 |
| h46A5 | 7 | 48 | 44 | 0 | 0 | 0 | 0 | 5.09 | 0 | 24.04 | 6.94 |
| h53A6 | 2 | 36 | 28 | 32 | 6.58 | 7.26 | 0 | 0 | 0 | 7.25 | 11.9 |
| h53B2 | 5 | 60 | 60 | 0 | 0 | 9.26 | 3.62 | 4.73 | 0 | 5.06 | 8.28 |
| h46A11 | 2 | 36 | 12 | 52 | 0 | 0 | 0 | 1.02 | 0 | 0 | 2.04 |
| h46A30/8 | 1 | 27 | 27 | 43 | 0 | 0 | 0 | 1.02 | 0 | 0 | 2.04 |
| h45A30/7 | 9 | 47 | 0 | 0 | 6.34 | 7.34 | 0 | 0.6 | 0 | 18.18 | 8.14 |
| h45A30/8 | 4 | 47 | 0 | 0 | 0 | 0 | 5.9 | 2.4 | 0 | 18.18 | 17.14 |
| h53A3 | 3 | 32 | 60 | 0 | 6.58 | 7.26 | 0 | 3.12 | 0 | 7.25 | 11.9 |
| h46A9 | 8 | 48 | 25 | 0 | 0 | 7.87 | 0 | 0 | 0 | 24.04 | 7.14 |
| h53B3 | 8 | 72 | 64 | 0 | 3.49 | 9.26 | 3.44 | 4.73 | 0 | 24.04 | 28.68 |
| h53D3 | 9 | 64 | 0 | 0 | 0 | 1.8 | 0 | 6.95 | 0 | 24.04 | 10.49 |
| h44B30/8 | 7 | 57 | 27 | 13 | 2.85 | 8.64 | 7.06 | 1.38 | 0 | 10.92 | 19.02 |
| h44B30/4 | 8 | 47 | 37 | 27 | 1.98 | 8.64 | 6.14 | 10.12 | 0 | 7.25 | 8.28 |
| h46A6 | 7 | 72 | 64 | 0 | 0 | 0 | 0 | 5.09 | 0 | 24.04 | 6.94 |
| h46A8 | 5 | 56 | 24 | 60 | 2.21 | 0 | 3.56 | 2.88 | 0 | 0 | 23.68 |
| h45A30/3 | 9 | 87 | 30 | 0 | 0 | 6.18 | 3.07 | 4.73 | 0.45 | 24.04 | 28.68 |
| h53D5 | 14 | 92 | 44 | 0 | 8.5 | 11.95 | 0 | 7.67 | 0.33 | 24.04 | 7.14 |
| h46A1 | 3 | 20 | 40 | 0 | 2.62 | 20.26 | 6.63 | 6.17 | 0 | 0 | 5.12 |
| h53A5 | 3 | 36 | 36 | 20 | 6.58 | 7.26 | 0 | 3.12 | 0 | 7.25 | 11.9 |
| h46A7 | 9 | 64 | 44 | 0 | 0 | 0 | 6.02 | 4.2 | 0 | 24.04 | 28.68 |
| h53A30/5 | 5 | 47 | 47 | 17 | 6.58 | 7.26 | 0 | 3.12 | 0 | 7.25 | 11.9 |
| h53A2 | 4 | 32 | 72 | 0 | 6.58 | 7.26 | 0 | 3.12 | 0 | 7.25 | 19.02 |
| h53A4 | 4 | 28 | 48 | 8 | 6.58 | 7.26 | 0 | 3.12 | 0 | 7.25 | 11.9 |
| h45A30/5 | 2 | 23 | 0 | 0 | 11.64 | 13.49 | 5.04 | 1.38 | 0 | 7.25 | 16.53 |
| h53D4 | 16 | 96 | 24 | 0 | 8.5 | 11.95 | 0 | 7.67 | 0.33 | 24.04 | 7.14 |
| h53A1 | 7 | 56 | 84 | 0 | 6.58 | 7.26 | 0 | 3.12 | 0 | 24.04 | 19.02 |
| A25 | 1 | 24 | 12 | 32 | 1.22 | 13.72 | 0 | 0 | 0 | 0 | 0 |
| h46A2 | 5 | 40 | 40 | 0 | 2.62 | 20.26 | 6.63 | 6.17 | 0 | 13.11 | 5.12 |
| h46A30/7 | 2 | 20 | 10 | 43 | 0 | 0 | 0 | 1.02 | 0 | 0 | 2.1 |
| h46A4 | 8 | 60 | 40 | 0 | 0 | 0 | 0 | 5.09 | 0 | 24.04 | 6.94 |

TABLE 1-continued

Table 1: Table summarizing the characteristics of PMOs used
PMOs are ranked in order of efficacy and characteristics of the PMOs and their target
sites listed.

| h44C30/2 | 3 | 33 | 10 | 63 | 0.52 | 5.72 | 0 | 0 | 0 | 9.46 | 5.6 |
|---|---|---|---|---|---|---|---|---|---|---|---|
| h44B30/7 | 6 | 40 | 30 | 27 | 2.85 | 8.64 | 7.06 | 1.38 | 0 | 10.92 | 19.02 |
| h51A | 2 | 40 | 3 | 27 | 1.22 | 13.72 | 0 | 0 | 0 | 0 | 4.45 |
| h44B30/6 | 8 | 37 | 20 | 27 | 2.85 | 8.64 | 0 | 1.92 | 0 | 10.92 | 19.02 |
| h44C30/3 | 2 | 33 | 0 | 63 | 0 | 0 | 0 | 6.44 | 0 | 9.46 | 5.6 |
| h44B30/1 | 6 | 67 | 33 | 30 | 0 | 0 | 6.14 | 10.12 | 0 | 10.92 | 8.28 |
| h53A30/6 | 5 | 48 | 37 | 27 | 6.58 | 7.26 | 0 | 3.12 | 0 | 7.25 | 11.9 |
| h53A30/4 | 4 | 43 | 57 | 7 | 6.58 | 7.26 | 0 | 3.12 | 0 | 7.25 | 11.9 |
| h44C30/1 | 3 | 43 | 27 | 63 | 0.52 | 5.72 | 7.06 | 0 | 0 | 9.46 | 5.6 |
| h46A3 | 5 | 40 | 40 | 0 | 2.62 | 20.26 | 6.63 | 6.17 | 0 | 13.11 | 5.12 |
| h44A30/3 | 3 | 23 | 0 | 77 | 0 | 13.26 | 0 | 0 | 0 | 0 | 11.3 |
| h53A30/1 | 9 | 60 | 86 | 0 | 6.58 | 7.26 | 0 | 3.12 | 0 | 24.04 | 19.02 |
| h44B30/3 | 5 | 47 | 37 | 33 | 0 | 0 | 6.14 | 10.12 | 0 | 7.25 | 8.28 |
| h44B30/5 | 10 | 63 | 37 | 27 | 1.98 | 8.64 | 6.14 | 1.92 | 0 | 10.92 | 19.02 |
| h45A30/1 | 2 | 0 | 0 | 6.7 | 3.43 | 8.64 | 5.16 | 3.54 | 3.57 | 0 | 20.56 |
| h46A30/3 | 5 | 40 | 33 | 0 | 0 | 0.57 | 0 | 6.17 | 0 | 13.11 | 5.12 |
| h46A30/1 | 5 | 33 | 33 | 0 | 2.62 | 20.26 | 6.63 | 6.17 | 0 | 13.11 | 5.12 |
| h46A30/5 | 12 | 67 | 50 | 0 | 0 | 0 | 0 | 5.09 | 0 | 24.04 | 6.94 |
| h53A30/3 | 6 | 43 | 67 | 0 | 6.58 | 7.26 | 0 | 3.12 | 0 | 24.04 | 19.02 |
| h44B30/2 | 5 | 50 | 37 | 37 | 0 | 0 | 6.14 | 10.12 | 0 | 7.25 | 8.28 |
| h53A30/2 | 8 | 53 | 77 | 0 | 6.58 | 7.26 | 0 | 3.12 | 0 | 24.04 | 19.02 |
| h46A30/4 | 8 | 50 | 43 | 0 | 0 | 0.57 | 0 | 5.09 | 0 | 24.04 | 5.12 |
| h46A30/2 | 5 | 33 | 33 | 0 | 2.62 | 20.26 | 6.63 | 6.17 | 0 | 13.11 | 5.12 |
| h45A30/2 | 0 | 0 | 0 | 20 | 3.43 | 10.41 | 5.16 | 3.54 | 3.57 | 0 | 20.56 |
| h44A30/2 | 3 | 27 | 0 | 63 | 0 | 13.26 | 0 | 0 | 0 | 0 | 11.3 |
| h44A30/1 | 4 | 43 | 0 | 47 | 0 | 13.26 | 0 | 2.76 | 0 | 0 | 11.3 |

[a] calculated as % skipped amplicon relative to total amplicon (i.e. skipped plus full length) as assessed by densitometric analysis of RT-PCR gels.
[b] calculated as % on PMO target site in open structures on predicted RNA secondary structure obtained using MFOLD analysis. The position of the PMO target sites relative to open loops in the RNA secondary structure is listed (0 = no ends in open loops, 1 = one end in an open loop, 2 = both ends in open loops).
[c] In analyses, SR binding sites were predicted using splice sequence finder (accessible on the world-wide web at umd.be/SSF/) software. Values above threshold are given for PMOs whose target sites cover 50% or more of potential SR binding sites for SF2/ASF, BRCA1, SC35, SRp40, SRp55, Tra2β and 9G8.

TABLE 2

Table 2: The correlation of significant design parameters and PMO target site properties to skipping efficacy
To establish the significance of design parameters and PMO target site properties to bioactivity, Mann-Whitney rank sum test analysis was
performed for each, comparing ineffective (inactive) PMOs to the different groups of PMOs, subdivided (in the column headed "Comparison")
according to bioactivity (efficacy). Criteria with p-values less than 0.05 in one or more comparisons are shown. The correlation of these
variables to bioactivity is confirmed by Spearman rank order test analysis, for which Spearman correlation coefficients and p-values are given.

| Comparison | PMO-target binding energy | % open conformation | Length | Distance from acceptor site | % overlap with hybridisation peak | % overlap with strongest hybrid. peak | % overlap with BRCA1 motif |
|---|---|---|---|---|---|---|---|
| Ineffective vs Effective | 0.001 | 0.094 | 0.017 | 0.004 | 0.056 | 0.003 | 0.026 |
| Ineffective vs 5-25% skip | 0.534 | 0.288 | 1 | 0.163 | 0.107 | 0.034 | 0.205 |
| Ineffective vs 25-50% skip | 0.02 | 0.316 | 0.014 | 0.067 | 0.614 | 0.195 | 0.079 |
| Ineffective vs 50-75% skip | 0.002 | 0.438 | 0.012 | 0.005 | 0.352 | 0.084 | 0.341 |
| Ineffective vs 75-100% skip | <0.001 | 0.025 | 0.002 | 0.003 | 0.045 | 0.002 | 0.091 |
| Ineffective vs >50% skip | <0.001 | 0.052 | <0.001 | <0.001 | 0.05 | 0.005 | 0.046 |
| Spearmans correlation coefficient | -0.618 | 0.275 | 0.545 | -0.421 | 0.258 | 0.46 | 0.261 |
| Spearmans p value | 0 | 0.0259 | 0 | 0 | 0.0363 | 0 | 0.0341 |

TABLE 3

Linear discriminant analysis of effective and ineffective PMOs
Linear discriminant analysis [34] was used to predict the classification
of PMOs on the basis of their PMO-target binding energy, overlap of
PMO target site with a hybridization peak, and overlap of PMO target
site with an ASF/SF2 (BRCA1) motif. PMOs have been grouped on
the basis of their experimental bioactivity ("Group" column), and
PMOs within each group predicted as "Effective" (bioactive) or
"Ineffective" (inactive), as indicated by the column headings,
according to the parameters used in the statistical analysis. The error
rate for wrongly classifying a PMO, and the average score are given
for each subgroup of PMO.

| Group | Classification Effective | Classification Ineffective | Total | Error rate | Average score |
|---|---|---|---|---|---|
| Effective | 40 | 4 | 44 | 0.09 | 0.741 |
| Ineffective | 9 | 13 | 22 | 0.41 | 0.512 |

TABLE 3-continued

Linear discriminant analysis of effective and ineffective PMOs
Linear discriminant analysis [34] was used to predict the classification
of PMOs on the basis of their PMO-target binding energy, overlap of
PMO target site with a hybridization peak, and overlap of PMO target
site with an ASF/SF2 (BRCA1) motif. PMOs have been grouped on
the basis of their experimental bioactivity ("Group" column), and
PMOs within each group predicted as "Effective" (bioactive) or
"Ineffective" (inactive), as indicated by the column headings,
according to the parameters used in the statistical analysis. The error
rate for wrongly classifying a PMO, and the average score are given
for each subgroup of PMO.

| Group | Classification Effective | Classification Ineffective | Total | Error rate | Average score |
|---|---|---|---|---|---|
| 0-5% skip | 9 | 13 | 22 | 0.41 | 0.512 |
| 5-25% skip | 16 | 4 | 20 | 0.2 | 0.621 |

TABLE 3-continued

Linear discriminant analysis of effective and ineffective PMOs
Linear discriminant analysis [34] was used to predict the classification
of PMOs on the basis of their PMO-target binding energy, overlap of
PMO target site with a hybridization peak, and overlap of PMO target
site with an ASF/SF2 (BRCA1) motif. PMOs have been grouped on
the basis of their experimental bioactivity ("Group" column), and
PMOs within each group predicted as "Effective" (bioactive) or
"Ineffective" (inactive), as indicated by the column headings,
according to the parameters used in the statistical analysis. The error
rate for wrongly classifying a PMO, and the average score are given
for each subgroup of PMO.

| Group | Classification | | Total | Error rate | Average score |
|---|---|---|---|---|---|
| | Effective | Ineffective | | | |
| 25-50% skip | 9 | 0 | 9 | 0 | 0.806 |
| 50-75% skip | 6 | 0 | 6 | 0 | 0.827 |
| 75-100% skip | 10 | 0 | 10 | 0 | 0.857 |

Example 2

Here, the inventors show the comparative analysis of a series of PMOs targeted to exon 53, skipping of which would have the potential to treat a further 8% of DMD patients with genomic deletions on the Leiden database compared to skipping of exon 51 which has the potential to treat 13% of DMD patients [37]. An array of overlapping PMOs were designed for the targeting of exon 53 as described previously [38]. These were all tested initially in normal human skeletal muscle cells (hSkMCs), since these are more readily available than patient cells. PMOs that showed greatest skipping efficacy were further tested in cells from a DMD patient with a relevant deletion (del 45-52). The PMOs with greatest efficacy, in terms of concentration and stability, were evaluated by performing dose-response and time-course studies. Findings from these experiments were supported by in vivo studies in a mouse model transgenic for the entire human dystrophin locus [8]. Collectively, this work suggests that one particular PMO (A, h53A30/1, +30+59) produced the most robust skipping of exon 53, and should be considered the sequence of choice for any upcoming PMO clinical trial.

MATERIALS AND METHODS

AO Design
Twenty-three overlapping AOs to exon 53 were designed as described above in Example 1.
Cell Culture and AO Transfection
Transfections were performed in two centres (Royal Holloway, London UK (RHUL) and UCL Institute of Child Health, London UK (UCL)) and by two different methods (liposome-carrier of leashed PMOs in normal cells (RHUL), and by nucleofection of naked PMOs in patient cells (UCL)). AOs were transfected into normal human primary muscle cells (TCS Cellworks, Buckingham, UK) and into patient primary skeletal muscle cultures obtained from muscle biopsies taken at the Dubowitz Neuromuscular Unit, UCL Institute of Child Health (London, UK), with the approval of the institutional ethics committee. Normal hSkMCs were cultured and transfected with leashed PMOs, using 1:4 lipofectin, as described previously [4]. To minimize any influence of leash design on PMO uptake and subsequent bioactivity, the DNA sequences in the leashes were of the same length (17 mers for the 25 mer PMOs or 20 mers for the 30 mer PMOs) and were completely complementary to the 3'-most 17 or 25 nt of each PMO. The phosphorothioate caps of 5 nt at each end were not complementary to the PMOs, and had the same sequences for every leash.

DMD Patient Primary Myoblast Culture
Skeletal muscle biopsy samples were taken from a diagnostic biopsy of the quadriceps from a DMD patient with a deletion of exons 45-52. Informed consent was obtained before any processing of samples. Muscle precursor cells were prepared from the biopsy sample by sharp dissection into 1 mm$^3$ pieces and disaggregated in solution containing HEPES (7.2 mg/ml), NaCl (7.6 mg/ml), KCl (0.224 mg/ml) Glucose (2 mg/ml) Phenol Red (1.1 µg/ml) 0.05% Trypsin-0.02% EDTA (Invitrogen, Paisley, UK) in distilled water, three times at 37° C. for 15 minutes in Wheaton flasks with vigorous stirring. Isolated cells were plated in non-coated plastic flasks and cultured in Skeletal Muscle Growth Media (Promocell, Heidelberg, Germany) supplemented with 10% Foetal Bovine Serum (PAA Laboratories, Yeovil, UK), 4 mM L-glutamine and 5 µg/ml gentamycin (Sigma-Aldrich, Poole, UK) at 37° C. in 5% $CO_2$.

Nucleofection of DMD Primary Myoblasts
Between $2\times10^5$ and $1\times10^6$ cells/ml were pelleted and resuspended in 100 µl of solution V (Amaxa Biosystems, Cologne, Germany). The appropriate PMO to skip exon 53 was added to the cuvette provided, sufficient to give the concentrations described, followed by the cell suspension, and nucleofected using the Amaxa nucleofector 2, program B32. 500 µl of media was added to the cuvette immediately following nucleofection. This suspension was transferred to a 6 well plate in differentiation medium. Nucleofected cells were maintained in differentiation media for 3-21 days post treatment before extraction of RNA or protein.

Lactate Dehydrogenase Cytotoxicity Assay
A sample of medium was taken 24 hours post-transfection to assess cytotoxicity by release of lactate dehydrogenase (LDH) into the medium, using the LDH Cytotoxicity Detection Kit (Roche, Burgess Hill, UK), following the manufacturer's instructions. The mean of three readings for each sample was recorded, with medium only, untreated and dead controls. The readings were normalised for background (minus medium only) and percentage toxicity expressed as [(sample-untreated)/(dead-untreated)×100].

RNA Isolation and Reverse Transcription-Polymerase Chain Reaction Analysis
As with cell culture, two different techniques were used in the two centres involved in this study for isolating RNA and its analysis by RT-PCR, as described previously [4]. PCR products were analysed on 1.5% (w/v) agarose gels in Tris-borate/EDTA buffer. Skipping efficiencies were determined by quantification of the full length and skipped PCR products by densitometry using GeneTools software (Syngene, Cambridge, UK).

Sequence Analysis
RT-PCR products were excised from agarose gels and extracted with a QIAquick gel extraction kit (Qiagen, Crawley, UK). Direct DNA sequencing was carried out by the MRC Genomics Core Facility.

Western Blot Analysis of Dystrophin Protein
DMD patient cells, transfected as described and cultured in differentiation medium, were harvested 7, 14 or 21 days post-transfection. $4\times10^5$ cells were pelleted and resuspended in 50 µl of loading buffer (75 mM Tris-HCl pH 6.8, 15% sodium dodecyl sulphate, 5% β-mercaptoethanol, 2% glycerol, 0.5% bromophenol blue and complete mini protease inhibitor tablet). Samples were incubated at 95° C. for 5 minutes and centrifuged at 18,000×g for 5 minutes. 20 µl of sample was loaded per well in a 6% polyacrylamide gel with 4% stacking gel. Protein from CHQSB cells differentiated for 7 days was used as a positive control for dystrophin. Gels were electrophoresed for 5 hours at 100V before blotting on nitrocellulose membrane at 200 mA overnight on ice. Blots were stained with Protogold to assess protein loading, then blocked in 10% non-fat milk in PBS with 2% tween (PBST) for 3 hours. Blots were probed with antibodies to dystrophin, NCL-DYS1 (Vector Labs, Peterborough, UK) diluted 1:40 and to dysferlin, Hamlet' (Vector Labs) diluted 1:300 in 3% non-fat milk/PBST. An anti-mouse, biotinylated secondary antibody (diluted 1:2000; GE Healthcare, Amersham, UK) and streptavidin/horse radish peroxidise conjugated antibody (1:10,000; Dako, Ely, UK) allowed visualisation in a luminol-HRP chemiluminescence reaction (ECL-Plus; GE Healthcare) on Hyperfilm (GE Healthcare), exposed at intervals from 10 seconds to 4 minutes.

Transgenic Human DMD Mice

A transgenic mouse expressing a complete copy of the human DMD gene has been generated [8, 39]. Experiments were performed at the Leiden University Medical Center, with the authorization of the Animal Experimental Commission (UDEC) of the Medical Faculty of Leiden University as described previously [4].

Results

Twenty-three PMOs were designed to target exon 53, as described previously [38]. Briefly, SR protein binding motifs, RNA secondary structure and accessibility to binding as determined by hexamer hybridization array analysis, were used as aids to design (FIGS. 1A-1F). Table 4 summarises the names and target sequence characteristics of these PMOs. These PMOs were initially characterized in normal human skeletal muscle cells (at RHUL). The most active were then directly compared to the PMO targeting the sequence previously identified as most bioactive by Wilton et al. [19] in exon 53-skippable patient cells (at UCL), and in the humanised DMD mouse (at LUMC).

Comparison of PMOs to Exon 53 in Normal Human Skeletal Muscle Cells

Figure 6A:
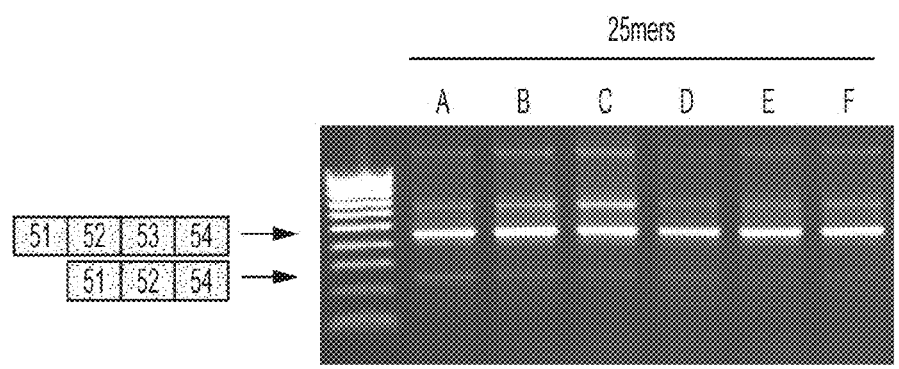
FIGS. 6A-6B show a comparison of bioactivity of PMOs targeted to exon 53 in normal hSkMCs. Myoblasts were transfected with each of the 25 mer (FIG. 6A) and 30 mer (FIG. 6B) PMOs indicated at 500 nM using lipofectin (1:4). RNA was harvested after 24 hours and subjected to nested RT-PCR and products visualised by agarose gel electrophoresis.

An array of seventeen 25 mer leashed PMOs were transfected, at a concentration of 500 nM, into normal human skeletal muscle myoblast cultures using lipofectin. Of these seventeen, only four produced consistent levels of exon skipping considered to be above background i.e. over 5% skipping [38], as assessed by densitometric analysis (FIG. 6A). These were PMO-A, -B, -C and -D, which targeted exon 53 at positions +35+59, +38+62, +41+65 and +44+68 respectively. The levels of exon skipping produced were as follows: PMO-A, 12.7%; PMO-B, 9.7%; PMO-C, 10.5%; and PMO-D, 9.0%. When nucleofection was used as a means of introducing naked PMOs into the cells, higher levels of exon skipping were observed for PMO-A and PMO-B only, with 300 nM doses producing 41.2% and 34.3% exon skipping, respectively. The superiority of nucleofection over lipofection has been observed by others (Wells et al., in preparation). However no exon skipping was evident following nucleofection with any of the other naked 25 mer PMOs tested (data not shown).

Figure 6B:
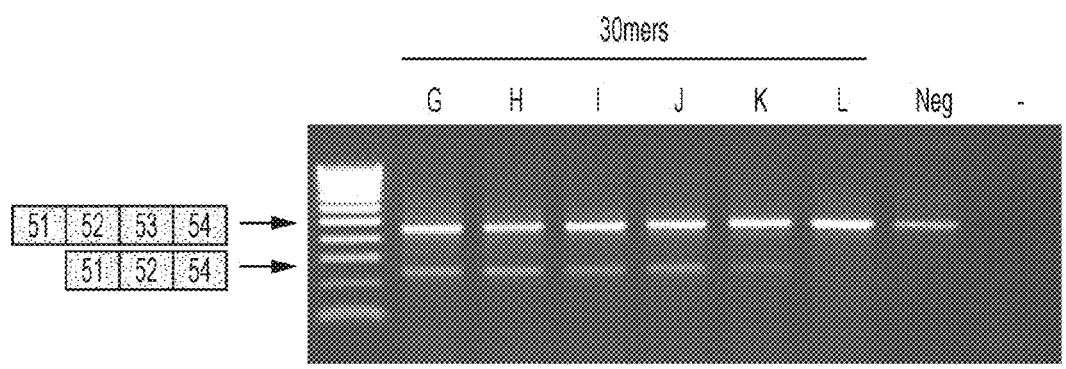
Figure 7A:
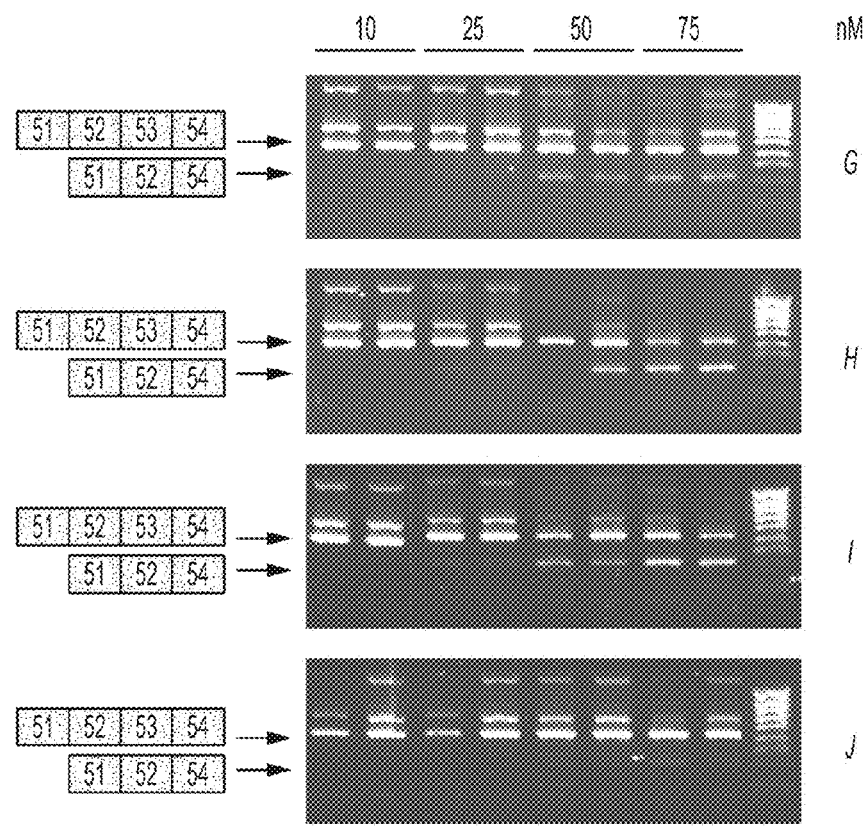
FIGS. 7A-7B show low dose efficacy and timecourse of skipping of the most bioactive PMOs in normal hSkMCs.
Figure 7B:
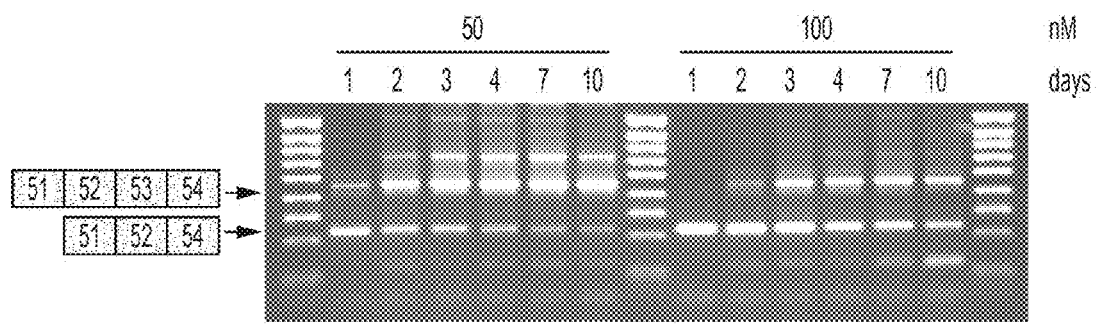

A 3 nt-stepped array of 30 mer PMOs was then designed to target the region of exon 53 (position +30 to +74) associated with exon skipping activity by the 25 mer PMOs. Following lipofection into normal human skeletal muscle myoblast cultures at a concentration of 500 nM, PMO-G (+30+59), PMO-H (+33+62), PMO-I (+36+65), PMO-J (+39+68) and PMO-K (+42+71) gave reproducible exon skipping above background (FIG. 6B), while PMO-L (+45+74) was inactive. The levels of exon skipping produced were as follows: PMO-G, 37.1%; PMO-H, 44.5%; PMO-I, 27.4%; PMO-J, 33.0%; and PMO-K, 13.0%. The concentration dependence of exon skipping by the more active 30 mer PMOs was examined further (FIG. 7A). PMO-H and PMO-I were able to produce convincing skipping at concentrations as low as 25 nM, while PMO-G was active at 50 nM and PMO-J at 75 nM. The exon skipping produced by these 30 mer PMOs was shown to be persistent, surviving the lifetime of the cultures (14 days) (FIG. 7B and data not shown). When unleashed 30 mer PMOs were introduced into normal muscle cultures by nucleofection, high levels of exon skipping were also observed. For example, at 300 nM, PMO-G and PMO-H gave over 80% skipping of exon 53 (data not shown).

Comparison of PMOs to Exon 53 in DMD Patient Cells

The PMOs, both 25 mer and 30 mer, that produced the highest levels of DMD exon 53 skipping in normal skeletal muscle cultures, were then compared to each other for bioactivity in DMD patient (del 45-52) cells, and were also compared to an additional reagent, PMO-M (+39+69), described previously [19]. This comparative evaluation was performed in a blinded fashion. When tested and compared directly at 300 nM doses by nucleofection, PMO-G, PMO-H and PMO-A were most active producing in the order of 60% exon skipping (FIGS. 8A-8B). The other PMOs tested produced the following exon skipping levels: PMO-I, 45%; PMO-B, 41%; PMO-J, 27%; PMO-M, 26%. All the other PMOs tested gave exon skipping at lower levels of between 10 and 20%.

Figure 9A:
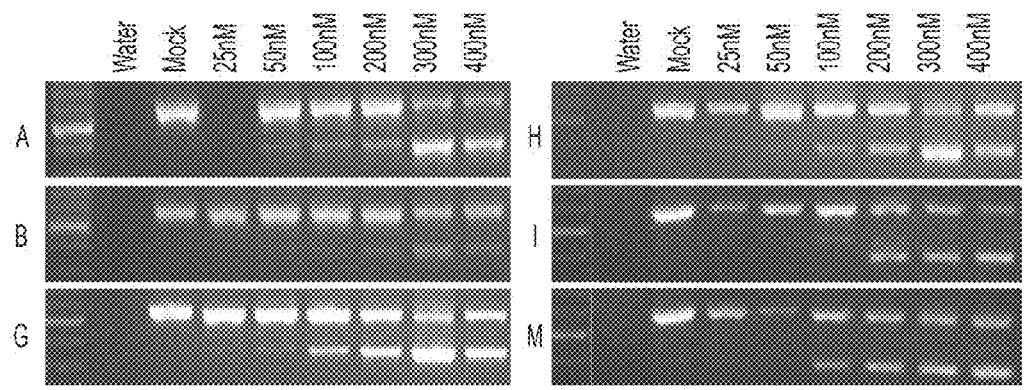
FIGS. 9A-9B show the dose-response of the six best-performing PMOs.
Figure 9B:
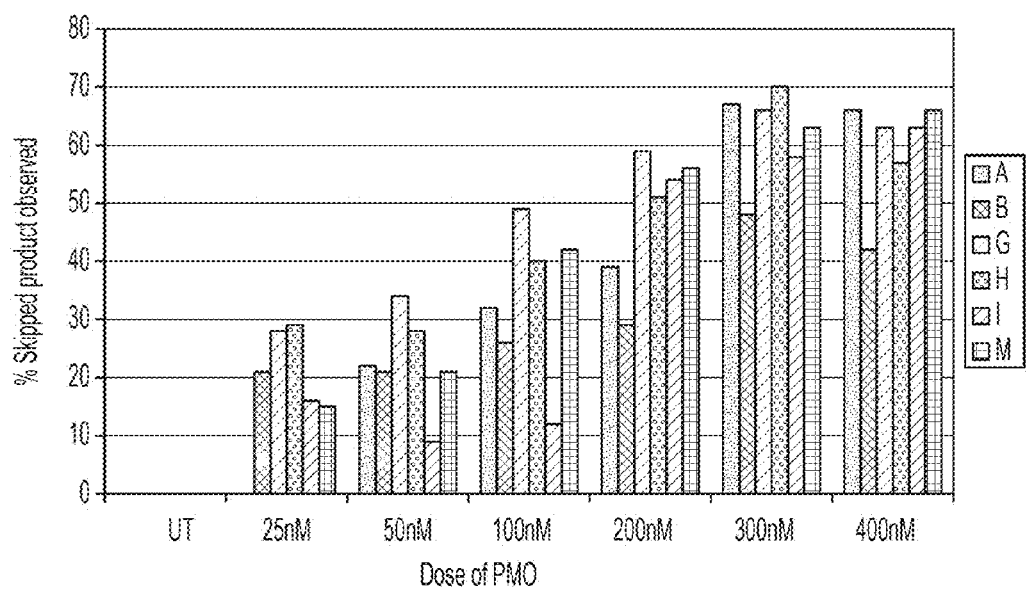

When the concentration dependence of exon skipping was examined for the most bioactive PMOs, levels approaching 30% were evident for PMO-G and PMO-H at concentrations as low as 25 nM (FIGS. 9A and 9B). Similar levels of skipping were only achieved by PMO-A, PMO-B and PMO-M at 100 nM, while PMO-I needed to be present at 200 nM to produce over 30% exon skipping (FIGS. 9A and 9B). There was no evidence that any of the PMOs tested caused cellular cytotoxicity relative to mock-transfected controls, as assessed by lactate dehydrogenase release into culture medium (results not shown). The exon skipping produced by the six most bioactive PMOs was shown to be persistent, lasting for up to 10 days after transfection, with over 60% exon skipping observed for the lifetime of the cultures for PMO-A, PMO-G and PMO-H (FIGS. 10A and 10B). Exon skipping was shown to persist for 21 days for PMO-A and PMO-G (FIG. 10C).

Western blot analysis of DMD patient (del 45-52) cell lysates, treated in culture with the most bioactive 25 mers (PMO-A and PMO-B) and longer PMOs (PMO-G, PMO-H, PMO-I and PMO-M) is shown in FIG. 10E. De novo expression of dystrophin protein was evident with all six PMOs, but was most pronounced with PMO-H, PMO-I, PMO-G and PMO-A, producing 50%, 45%, 33% and 26% dystrophin expression, respectively, relative to the positive control, and seemingly weakest with PMO-B and PMO-M (11% and 17% dystrophin expression respectively, relative to the positive control). However, the limitations of quantifying Western blots of this nature should be taken into account when interpreting the data.

Comparison of PMOs to Exon 53 in Humanised DMD Mouse

Figure 11:
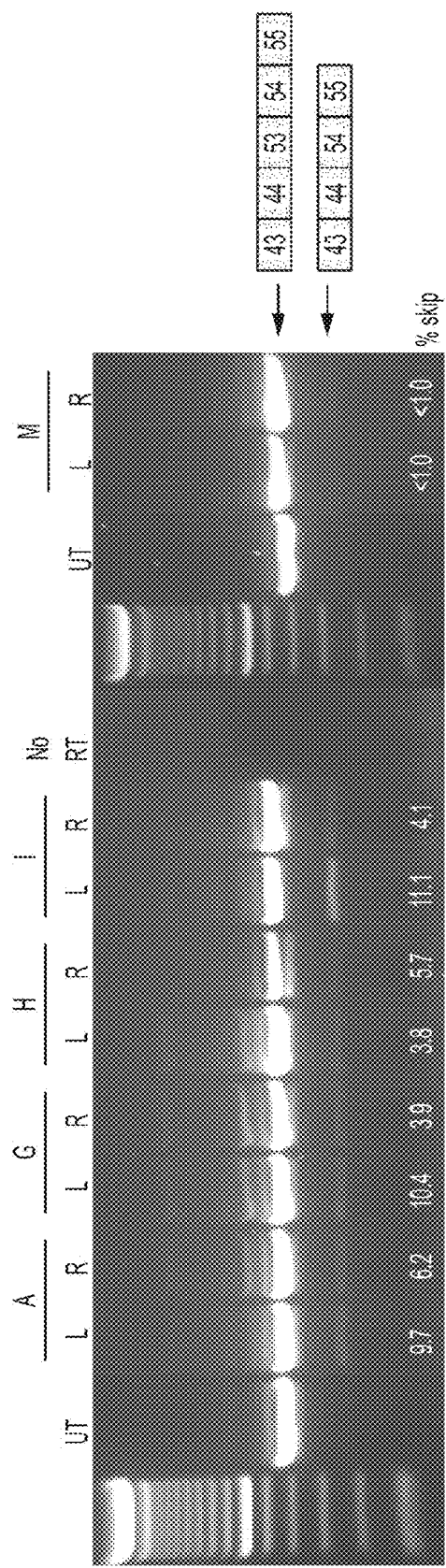
FIG. 11 shows a comparison of most active PMOs in hDMD mice. PMOs were injected in a blind experiment into the gastrocnemius muscle of hDMD mice. RT-PCR analysis of RNA harvested from isolated muscle (L=left, R=right) was performed and products visualised by agarose gel electrophoresis. Quantification of PCR products was performed using a DNA LabChip.

The hDMD mouse is a valuable tool for studying the processing of the human DMD gene in vivo, and as such provides a model for studying the in vivo action of PMOs, prior to clinical testing in patients. PMO-A, PMO-G, PMO-H, PMO-I and PMO-M were injected into the gastrocnemius muscle of hDMD mice, and RNA extracted from the muscles was analysed for exon 53 skipping (FIG. 11). Skipping of exon 53 is evident for each of the PMOs tested; 8% for PMO-A, 7.6% for PMO-I, 7.2% for PMO-G, but to a slightly lower level of 4.8% for PMO-H. PMO-M produced exon skipping levels of less than 1%, which is the detection threshold for the system used.

It should be noted that the levels of exon skipping by each particular PMO was variable. This has been reported previously [8], and is likely to be due to the poor uptake into the non-dystrophic muscle of the hDMD mouse. However this does not compromise the importance of the finding that the PMOs tested here are able to elicit the targeted skipping of exon 53 in vivo.

Of the 24 PMOs tested, six (PMO-A, PMO-B, PMO-G, PMO-H, PMO-I and PMO-M) produced over 50% targeted skipping of exon 53 either in normal myotubes or in patient myotubes or both. The characteristics of these active PMOs and their target sites are summarised in Table 4. They all showed strong overlap (92%-100%) with the sequence shown to be accessible to binding on the hybridization array analysis, had similar GC content (50%-56%), but varying degrees of overlap (32%-60%) with ESE sites as predicted by Rescue ESE analysis, varying degrees of overlap with ESE sites and ESS sites (60%-86% and 0%-10%, respectively) as predicted by PESX analysis, and all showed overlap with two SR binding motifs (SF2/ASF, as defined by the BRCA1 algorithm, and SRp40). It should be noted that PMO-J, -K, -L and -M had a common SNP of exon 53 (c7728C>T) in the last, fourth to last, seventh to last and second to last base, respectively of their target sites. There is the potential that this allelic mismatch could influence the binding and bioactivity of these PMOs. However, the more active PMOs (-A, -B, -G, -H and -I) all had their target sites away from the SNP, and the possible effect of a mismatch weakening binding and bioactivity is removed, and allows definitive comparisons between these PMOs to be made.

Discussion

The putative use of AOs to skip the exons which flank out-of-frame deletions is fast becoming a reality in the experimental intervention of DMD boys. Indeed the restoration of dystrophin expression in the TA muscle of four patients, injected with a 2'OMePS AO optimised to target exon 51 of the DMD gene, has been reported recently [11]. Moreover a clinical trial using a PMO targeting exon 51 has recently been completed in seven DMD boys in the UK (Muntoni et al, in preparation). However, the targeted skipping of exon 51 would have the potential to treat only 13% of DMD patients with genomic deletions on the Leiden database [37]. There is therefore a definite requirement for the optimisation of AOs to target other exons commonly mutated in DMD.

Although there have been many large screens of AO bioactivity in vitro [18, 19, 38, 40], no definite rules to guide AO design have become apparent. Previous studies in the mdx mouse model of DMD showed that AOs that targeted the donor splice site of exon 23 of the mouse DMD gene restored dystrophin expression [7]. However the targeting of AOs to the donor splice sites of exon 51 of the human DMD gene was ineffective at producing skipping [4], and it has been suggested that the 'skippability' of human DMD exons has no correlation with the predicted strength of the donor splice site [41]. It has been reported that exon skipping could be induced by the targeting of AOs to exonic splicing enhancer (ESE) motifs [18, 40]. These motifs are recognised by SR proteins, which facilitate exon splicing by recruiting splicing effectors (U1 and U2AF) to the donor splice site (reviewed by Cartegni et al.) [42]. However these motifs are divergent, poorly defined, their identification complex, and their strength as AO design tools dubious [38].

A comparative study of 66 PMOs designed to five different DMD exons demonstrated the significance of RNA secondary structure in relation to accessibility of the PMO target site and subsequent PMO bioactivity [38], as assessed by mfold software prediction of secondary structure [25], and a hybridization screen against a hexamer array [38]. PMOs that bound to their target more strongly, either as a result of being longer or in being able to access their target site more directly, were significantly more bioactive. The influence of AO length on bioactivity has been reported elsewhere [4, 30], and is further confirmed in the present study; all 30 mers tested were more bioactive relative to their 25 mer counterpart. The fact that 30 mer PMOs were more bioactive than 25 mer PMOs targeted to the same open/accessible sites on the exon, would suggest that strength of binding of PMO to the target site may be the most important factor in determining PMO bioactivity. These thermodynamic considerations have also been reported in a complementary study of 2'OMePS AOs [40]. However, it has also been reported that two overlapping 30 mers were not as efficient as a 25 mer at skipping mouse exon 23, indicating that oligomer length may only be important in some cases [4].

To ensure that the analysis of PMOs for the targeted skipping of exon 53 was not biased by any particular design strategy, seventeen 25 mer PMOs were designed to cover the whole of exon 53, with stepwise arrays over suggested bioactive target sites, and then subsequently six 30 mer PMOs were designed to target the sequence of exon 53 that showed an association with exon skipping for the 25 mers tested. PMOs were designed and tested independently by two different groups (at RHUL and UWA), and then efficacy of the best thirteen sequences confirmed by two other independent groups (at UCL and LUMC). Such a collaborative approach has been used previously as a way of validating target sequences in DMD [4]. Human myoblasts allowed the controlled in vitro comparison of PMO sequences, and confirmation of skipping of exon 53 at the RNA level by certain PMOs in both normal cells and, perhaps more importantly, in DMD patient cells with a relevant mutation. These results were further borne out by the expression of dystrophin protein in the DMD cells treated with specific PMOs. Use of the humanised DMD mouse provided an in vivo setting to confirm correct exon exclusion prior to any planned clinical trial. The combined use of these three different systems (normal cells, patient cells and hDMD mouse) as tests of PMO bioactivity provided a reliable and coherent determination of optimal sequence(s) for the targeted skipping of exon 53.

When considering the data presented here as a whole, the superiority of the PMO targeting the sequence +30+59 (PMO-G, or h53A30/1), is strongly indicated. In normal myoblasts, nucleofection of PMO-G (300 nM) and liposomal-carrier mediated transfection of leashed PMO-G (500 nM) produced over 80% and over 50% skipping of exon 53, respectively, implying that it acts extremely efficiently within the cell.

This was confirmed in patient cells. Indeed, this PMO generates the highest levels of exon skipping in patient cells over a range of concentrations (up to 200 nM) and, most important therapeutically, exerts its activity at concentrations as low as 25 nM. The exon skipping activity of this PMO is also persistent, with over 70% exon skipping for 7 days in culture, and over 60% exon skipping for up to three weeks. This would have important safety and cost implications as a genetic therapy for DMD patients with the appropriate deletions. PMO-G was also shown to skip exon 53 correctly in vivo. These RNA results were further confirmed by the detection of dystrophin protein at a high level in protein extracts from patient cells treated with PMO-G. Previous studies by the Leiden group [18] suggest that the optimal 2'OMePS AO is targeted to the sequence +46+63 of exon 53, producing exon skipping in up to 25% of transcripts in cultured cells and 7% in the hDMD mouse. This 2'OMePS AO shows some degree of overlap with the optimal PMOs reported here which strengthens our findings. The reason that our optimal PMO is more specific could be a (combined) consequence of the different AO chemistries, length of AO used, and the absolute target site of AO.

The sequence h53A30/1 we have identified appears to be more efficient than any of the previously reported AOs designed to skip exon 53 of the DMD gene, and this PMO therefore represents, at the present time, the optimal sequence for clinical trials in DMD boys.

Table 4: Table Summarizing the Characteristics of PMOs Used

Characteristics of the PMOs and their Target Sites Listed.

[b] calculated as % of PMO target site in open structures on predicted RNA secondary structure obtained using MFOLD analysis. The position of the PMO target sites relative to open loops in the RNA secondary structure is listed (0=no ends in open loops, 1=one end in an open loop, 2=both ends in open loops).

[c] In the analyses, SR binding sites were predicted using splice sequence finder (accessible on the world-wide web at umd.be/SSF/) software. Values above threshold are given for PMOs whose target sites cover 50% or more of potential binding sites for SF2/ASF, BRCA1, SC35, SRp40, SRp55, Tra2β and 9G8

TABLE 4

|   | PMO | Position Start | Position End | % GC | Exon-PMO binding energy | PMO-PMO binding energy | % open[b] | Ends in open loops[b] | % overlap with hybrid. peak | # Rescue ESE sites | % overlap with Rescue ESE |
|---|---|---|---|---|---|---|---|---|---|---|---|
| A | h53A1 | +35 | +59 | 52 | −38.6 | −17.4 | 50 | 2 | 92 | 7 | 56 |
| B | h53A2 | +38 | +62 | 56 | −36.1 | −17.4 | 46.7 | 1 | 100 | 4 | 32 |
| C | h53A3 | +41 | +65 | 56 | −36.7 | −13.7 | 36.7 | 0 | 0 | 3 | 32 |
| D | h53A4 | +44 | +68 | 48 | −34.3 | −8.5 | 20 | 0 | 100 | 4 | 28 |
| E | h53A5 | +47 | +71 | 48 | −35.5 | −8.5 | 43.3 | 2 | 100 | 3 | 36 |
| F | h53A6 | +50 | +74 | 48 | −35.3 | −8.5 | 43.3 | 2 | 92 | 2 | 36 |
| N | h53B1 | +69 | +93 | 28 | −22.1 | −12.1 | 53.3 | 1 | 0 | 5 | 56 |
| O | h53B2 | +80 | +104 | 48 | −30.1 | −11.3 | 23.3 | 1 | 0 | 5 | 60 |
| P | h53B3 | +90 | +114 | 48 | −34.5 | −5.5 | 48 | 2 | 0 | 8 | 72 |
| Q | h53C1 | +109 | +133 | 48 | −32.4 | −9.8 | 46.7 | 2 | 0 | 6 | 52 |
| R | h53C2 | +116 | +140 | 56 | −31.3 | −12.7 | 33.3 | 1 | 0 | 1 | 24 |
| S | h53C3 | +128 | +152 | 60 | −34.6 | −13.7 | 26.7 | 1 | 0 | 1 | 24 |
| T | h53D1 | +149 | +173 | 52 | −34.1 | −13.4 | 30 | 1 | 0 | 4 | 40 |
| U | h53D2 | +158 | +182 | 48 | −36.5 | −14.5 | 40 | 2 | 0 | 6 | 44 |
| V | h53D3 | +170 | +194 | 36 | −34.3 | −11.2 | 40 | 1 | 0 | 9 | 64 |
| W | h53D4 | +182 | +206 | 32 | −30.9 | −9.2 | 63.3 | 1 | 0 | 16 | 96 |
| X | h53D5 | +188 | +212 | 36 | −31.5 | −3.3 | 66.7 | 1 | 0 | 14 | 92 |
| G | h53A30/1 | +30 | +59 | 50 | −48.1 | −17.4 | 56.7 | 1 | 92 | 9 | 60 |
| H | h53A30/2 | +33 | +62 | 53 | −45.1 | −17.4 | 63.3 | 1 | 100 | 8 | 53 |
| I | h53A30/3 | +36 | +65 | 53 | −44.6 | −17.4 | 53.3 | 1 | 100 | 6 | 43 |
| J | h53A30/4 | +39 | +68 | 50 | −43.4 | −17.4 | 43.3 | 1 | 100 | 4 | 43 |
| K | h53A30/5 | +42 | +71 | 47 | −42.4 | −11.3 | 46.7 | 1 | 100 | 5 | 47 |
| L | h53A30/6 | +45 | +74 | 47 | −42.3 | −8.5 | 56.7 | 1 | 100 | 5 | 48 |
| M | H53A | +39 | +69 | 52 | −48.5 | −17.4 | 48.4 | 2 | 100 | 4 | 45 |

|   | PMO | % overlap with PESE | % overlap with PESS | ESE finder values over threshold[c] SF2/ASF | BRCA1 | SC35 | SRp40 | SRp55 | Tra2B | 9G8 |
|---|---|---|---|---|---|---|---|---|---|---|
| A | h53A1 | 84 | 0 | 6.58 | 7.26 | 0 | 3.12 | 0 | 24.04 | 19.02 |
| B | h53A2 | 72 | 0 | 6.58 | 7.26 | 0 | 3.12 | 0 | 7.25 | 19.02 |
| C | h53A3 | 60 | 0 | 6.58 | 7.26 | 0 | 3.12 | 0 | 7.25 | 11.9 |
| D | h53A4 | 48 | 8 | 6.58 | 7.26 | 0 | 3.12 | 0 | 7.25 | 11.9 |
| E | h53A5 | 36 | 20 | 6.58 | 7.26 | 0 | 3.12 | 0 | 7.25 | 11.9 |
| F | h53A6 | 28 | 32 | 6.58 | 7.26 | 0 | 0 | 0 | 7.25 | 11.9 |
| N | h53B1 | 40 | 40 | 0 | 9.26 | 3.62 | 10.66 | 0 | 5.06 | 1.1 |
| O | h53B2 | 60 | 0 | 0 | 9.26 | 3.62 | 4.73 | 0 | 5.06 | 8.28 |
| P | h53B3 | 64 | 0 | 3.49 | 9.26 | 3.44 | 4.73 | 0 | 24.04 | 28.68 |
| Q | h53C1 | 72 | 0 | 4.19 | 6.72 | 0 | 2.04 | 0 | 24.04 | 28.68 |
| R | h53C2 | 60 | 0 | 4.19 | 6.72 | 10.2 | 4.38 | 0 | 0 | 8.28 |
| S | h53C3 | 32 | 0 | 3.49 | 6.41 | 10.2 | 4.38 | 6.86 | 0 | 14.18 |
| T | h53D1 | 32 | 0 | 0.52 | 0 | 18.68 | 0 | 6.86 | 0 | 12.71 |
| U | h53D2 | 32 | 0 | 0.52 | 1.8 | 18.68 | 0.42 | 0 | 0 | 12.71 |
| V | h53D3 | 0 | 0 | 0 | 1.8 | 0 | 6.95 | 0 | 24.04 | 10.49 |
| W | h53D4 | 24 | 0 | 8.5 | 11.95 | 0 | 7.67 | 0.33 | 24.04 | 7.14 |
| X | h53D5 | 44 | 0 | 8.5 | 11.95 | 0 | 7.67 | 0.33 | 24.04 | 7.14 |
| G | h53A30/1 | 86 | 0 | 6.58 | 7.26 | 0 | 3.12 | 0 | 24.04 | 19.02 |
| H | h53A30/2 | 77 | 0 | 6.58 | 7.26 | 0 | 3.12 | 0 | 24.04 | 19.02 |
| I | h53A30/3 | 67 | 0 | 6.58 | 7.26 | 0 | 3.12 | 0 | 24.04 | 19.02 |
| J | h53A30/4 | 57 | 7 | 6.58 | 7.26 | 0 | 3.12 | 0 | 7.25 | 11.9 |

TABLE 4-continued

| | | | | | | | | | |
|---|---|---|---|---|---|---|---|---|---|
| K | h53A30/5 | 47 | 17 | 6.58 | 7.26 | 0 | 3.12 | 0 | 7.25 | 11.9 |
| L | h53A30/6 | 37 | 27 | 6.58 | 7.26 | 0 | 3.12 | 0 | 7.25 | 11.9 |
| M | H53A | 58 | 10 | 6.58 | 7.26 | 0 | 3.12 | 0 | 7.25 | 11.9 |

REFERENCES

1. Hoffmann E P, Brown R H, Kunkel L M (1987) Dystrophin: The protein product of the Duchenne muscular dystrophy locus. *Cell;* 51: 919-928.
2. Den Dunnen J T, Grootscholten P M, Bakker E, Blonden L A, Ginjaar H B, Wapenaar M C, et al. (1989). Topography of the Duchenne muscular dystrophy (DMD) gene: FIGE and cDNA analysis of 194 cases reveals 115 deletions and 13 duplications. *Am J Hum Genet;* 45: 835-847.
3. van Deutekom J C, Bremmer-Bout M, Janson A A, Ginjaar I B, Baas F, den Dunnen J T, et al. (2001). Antisense-induced exon skipping restores dystrophin expression in DMD patient derived muscle cells. *Hum Mol Genet;* 10: 1547-1554.
4. Arechavala-Gomeza V, Graham I R, Popplewell L J, Adams A M, Aartsma-Rus A, Kinali M, et al. (2007). Comparative analysis of antisense oligonucleotide sequences for targeted skipping of exon 51 during pre-mRNA splicing in human muscle. *Hum Gene Ther;* 18: 798-810.
5. Mann C J, Honeyman K, Cheng A J, Ly T, Lloyd F, Fletcher S, et al. (2001). Antisense-induced exon skipping and synthesis of dystrophin in the mdx mouse. *Proc Natl Acad Sci USA;* 98: 42-47.
6. Lu Q L, Mann C J, Lou F, Bou-Gharios G, Morris G E, Xue S A, et al. (2003). Functional amounts of dystrophin produced by skipping the mutated exon in the mdx dystrophic mouse. *Nat Med;* 9: 1009-1014.
7. Graham I R, Hill V J, Manoharan M, Inamati G B, Dickson G (2004). Towards a therapeutic inhibition of dystrophin exon 23 splicing in mdx mouse muscle induced by antisense oligonucleotides (splicomers): target sequence optimisation using oligonucleotide arrays. *J Gene Med;* 6: 1149-1158.
8. Bremmer-Bout M, Aartsma-Rus A, de Meijer E J, Kaman W E, Janson A A, Vossen R H, et al. (2004). Targeted exon skipping in transgenic hDMD mice: A model for direct preclinical screening of human-specific antisense oligonucleotides. *Mol Ther;* 10: 232-240
9. Jearawiriyapaisarn N, Moulton H M, Buckley B, Roberts J, Sazani P, Fucharoen S, et al. (2008). Sustained dystrophin expression induced by peptide-conjugated morpholino oligomers in the muscles of mdx mice. *Mol Ther.* June 10 (Epub).
10. Bertoni C. (2008). Clinical approaches in the treatment of Duchenne muscular dystrophy (DMD) using oligonucleotides. *Front Biosci;* 13: 517-527.
11. van Deutekom J C, Janson A A, Ginjaar I B, Franzhuzen W S, Aartsma-Rus A, Bremmer-Bout M, et al. (2007). Local antisense dystrophin restoration with antisense oligonucleotide PRO051. *N Eng J Med;* 357: 2677-2687.
12. Gebski B L, Mann C J, Fletcher S, Wilton S D (2003). Morpholino antisense oligonucleotide induced dystrophin exon 23 skipping in mdx mouse muscle. Hum *Mol Genet;* 12: 1801-1811.
13. Alter J, Lou F, Rabinowitz A, Yin H, Rosenfeld J, Wilton S D, et al. (2006). Systemic delivery of morpholino oligonucleotide restores dystrophin expression bodywide and improves dystrophic pathology. *Nat Med;* 12: 175-177.
14. Fletcher S, Honeyman K, Fall A M, Harding P L, Johnsen R D, Wilton S D (2006). Dystrophin expression in the mdx mouse after localized and systemic administration of a morpholino antisense oligonucleotide. *J Gene Med;* 8: 207-216.
15. McClorey G, Fall A M, Moulton H M, Iversen P L, Rasko J E, Ryan M, et al. (2006). Induced dystrophin exon skipping in human muscle explants. *Neuromus Disorders;* 16: 583-590.
16. McClorey G, Moulton H M, Iversen P L, Fletcher S, Wilton S D (2006). Antisense oligonucleotide-induced exon skipping restores dystrophin expression in vitro in a canine model of DMD. *Gene Ther;* 13:1373-1381.
17. Arora V, Devi G R, Iversen P L (2004). Neutrally charged phosphorodiamidate morpholino antisense oligomers: uptake, efficacy and pharmacokinetics. *Curr Pharm Biotechnol;* 5: 431-439.
18. Aartsma-Rus A, De Winter C L, Janson A A M, Kaman W E, van Ommen G-J B, Den Dunnen J T, et al. (2005). Functional analysis of 114 exon-internal AONs for targeted DMD exon skipping: Indication for steric hindrance of SR protein binding sites. *Oligonucleotides;* 15: 284-297.
19. Wilton S D, Fall A M, Harding P L, McClorey G, Coleman C, Fletcher S (2007). Antisense oligonucleotide-induced exon skipping across the human dystrophin gene transcript. *Mol Ther;* 15: 1288-1296.
20. Cartegni L, Wang J, Zhu Z, Zhang M Q, Krainer A R (2003). ESEfinder: A web resource to identify exonic splicing enhancers. *Nucleic Acids Res;* 31: 3568-3571.
21. Smith P J, Zhang C, Wang J, Chew S L, Zhang M O, Krainer A R (2006). An increased specificity score matrix for the prediction of SF2/ASF-specific exonic splicing enhancers. *Human Mol Genet;* 15: 2490-2508.
22. Zhang X H, Chasin L H (2004). Computational definition of sequence motifs governing constitutive exon splicing. *Genes Dev;* 18: 1241-1250.
23. Zhang X H, Leslie C S, Chasin L A (2005). Computational searches for splicing signals. *Methods;* 37: 292-305.
24. Fairbrother W G, Yeh R F, Sharp P A, Burge C B (2002). Predictive identification of exonic splicing enhancers in human genes. *Science;* 297: 1007-1013.
25. Mathews D H, Sabina J, Zuker M, Turner D H (1999). Expanded sequence dependence of thermodynamic parameters improves prediction of RNA secondary structure. *J Mol Biol;* 288: 911-940.
26. Aartsma-Rus A, Bremmer-Bout M, Janson A A M, den Dunnen J T, van Ommen G-J B, van Deutekom J C T (2002). Targeted exon skipping as a potential gene correction therapy for Duchenne muscular dystrophy. *Neuromus Disorders;* 12: 871-877.
27. Aartsma-Rus A, Kaman W E, Weij R, den Dunnen J T, van Ommen G J, van Deutekom J C. (2006). Exploring the frontiers of therapeutic exon skipping for Duchenne muscular dystrophy by double targeting within one or multiple exons. *Mol Ther;* 14: 401-407.

28. Adams A M, Harding P L, Iversen P L, Coleman C, Fletcher S, Wilton S D. (2007). Antisense oligonucleotide induced exon skipping and the dystrophin gene transcript: cocktails and chemistries. *BMC Mol Biol;* 8: 57.
29. Vickers T A, Wyatt J R, Freier S M (2000). Effects of RNA secondary structure on cellular antisense activity. *Nucleic Acids Res;* 28: 1340-1347.
30. Harding P L, Fall A M, Honeyman K, Fletcher S, Wilton S D (2007). The influence of antisense oligonucleotide length on dystrophin exon skipping. *Mol Ther;* 15: 157-166.
31. Wee K B, Pramono Z A D, Wang J L, MacDorman K F, Lai P S, Yee W C (2008). Dynamics of co-translational pre-mRNA folding influences the induction of dystrophin exon skipping by antisense oligonucleotides. *Plos one;* 3: e1844.
32. Fairbrother W G, Yeo G W, Yeh R, Goldstein P, Mawson M, Sharp P A, et al. (2004). RESCUE-ESE identifies candidate exonic splicing enhancers in vertebrate exons. *Nucleic Acids Res;* 32: W187-190.
33. Patzel V, Steidl R, Kronenwell R, Haas R, Sczakiel G (1999). A theoretical approach to select effective antisense oligodeoxyribonucleotides at high statistical probability. Nucleic Acids Res; 27: 4328-4334.
34. Ihaka R, Gentleman R C (1996). R: A Language for Data Analysis and Graphics. *Journal of Computational and Graphical Statistics;* 15: 999-1013.
35. Moulton H M, Fletcher S, Neuman B W, McClorey G, Stein D A, Abes S, Wilton S D, Buchmeier M J, Lebleu B, Iversen P L (2007). Cell-penetrating peptide-morpholino conjugates alter pre-mRNA splicing of DMD (Duchenne muscular dystrophy) and inhibit murine coronavirus replication in vivo. *Biochem. Soc. Trans.* 35: 826-8.
36. Jearawiriyapaisarn N, Moulton H M, Buckley B, Roberts J, Sazani P, Fucharoen S, Iversen P L, Kole R (2008). Sustained Dystrophin Expression Induced by Peptide-conjugated Morpholino Oligomers in the Muscles of mdx Mice. *Mol. Ther.* June 10. Epub ahead of print.
37. Aartsma-Rus A, Fokkema I, Verschuuren J, Ginjaar I, van Deutekom J, van Ommen G J et al. Theoretic applicability of antisense-mediated exon skipping for Duchenne muscular dystrophy mutations. *Hum Mutation* 2009; January 20 (Epub).
38. Popplewell L J, Trollet C, Dickson G, Graham I R. Design of phosphorodiamidate morpholino oligomers (PMOs) for the induction of exon skipping of the human DMD gene. *Mol Ther* 2009; January 13 (Epub).
39. 'tHoen P A C, de Meijer E J, Boer J M, Vossen R H, Turk R, Maatman R G et al. (2008) Generation and characterization of transgenic mice with the full-length human DMD gene. *J Biol Chem;* 283: 5899-5907.
40. Aartsma-Rus A, van Vliet L, Hirschi M, Janson A A, Heemskerk H, de Winter C L, et al. Guidelines for antisense oligonucleotide design and insight into splice-modulating mechanisms. *Mol Ther* 2008; September 23 (Epub).
41. Aartsma-Rus A, van Ommen G J. Antisense-mediated exon skipping: A versatile tool with therapeutic and research applications. *RNA* 2007; 13: 1-16.
42. Cartegni L, Chew S L, Krainer A R. Listening to silence and understanding nonsense: Exonic mutations that affect splicing. *Nat Rev Genet* 2002; 3: 285-298.

---

The invention claimed is:

1. An oligomer for ameliorating Duchenne muscular dystrophy (DMD), the oligomer comprising at least 25 contiguous bases of:

a)
(SEQ ID NO: 10)
CXG XXG CCX CCG GXX CXG AAG GXG XXC XXG;
or b)
(SEQ ID NO: 12)
XXG CCX CCG GXX CXG AAG GXG XXC XXG XAC;

wherein X=U or T, wherein the sequence of the at least 25 contiguous bases can vary from SEQ ID NO: 10 or 12 at up to two base positions, and wherein the oligomer comprises one or more synthetically modified nucleotides.

2. The oligomer according to claim 1, wherein the oligomer can bind to a target site to cause exon skipping of exon 53 of the dystrophin gene.

3. The oligomer according to claim 1, wherein the oligomer can bind to a target site to cause exon skipping of an exon of the dystrophin gene at a rate of at least 50%.

4. The oligomer according to claim 1, wherein the oligomer can bind to a target site to cause exon skipping of an exon of the dystrophin gene at a rate of at least 70%.

5. The oligomer according to claim 1, wherein the oligomer can bind to a target site to cause exon skipping of an exon of the dystrophin gene at a rate of at least 90%.

6. The oligomer according to claim 1, wherein the one or more synthetically modified nucleotides are modified at the 2' position of the ribose.

7. The oligomer according to claim 6, wherein the one or more synthetically modified nucleotides are 2'-O-methyl oligonucleotide.

8. The oligomer according to claim 1, wherein the one or more synthetically modified nucleotides are a phosphorodiamidate morpholino oligonucleotide.

9. The oligomer according to claim 1, wherein the oligomer is at least 28 and at most 32 bases in length.

10. The oligomer according to claim 1, wherein the oligomer is at least 29 and at most 31 bases in length.

11. The oligomer according to claim 1, wherein the oligomer is conjugated to or complexed with a targeting protein that targets the oligomer to muscle tissue.

12. The oligomer according to claim 1, wherein the oligomer is conjugated to or complexed with a drug for treating Duchenne muscular dystrophy.

13. The oligomer according to claim 1, wherein the oligomer is conjugated to or complexed with an arginine-rich cell penetrating peptide.

14. A pharmaceutical composition for ameliorating DMD, the composition comprising an oligomer according to claim 1, and a pharmaceutically acceptable carrier, adjuvant or vehicle.

* * * * *